US009655963B2

(12) United States Patent
Suzuki et al.

(10) Patent No.: US 9,655,963 B2
(45) Date of Patent: May 23, 2017

(54) DIAGNOSING AND TREATING IGA NEPHROPATHY

(71) Applicants: THE UAB RESEARCH FOUNDATION, Birmingham, AL (US); US ARMY WALTER REED ARMY MEDICAL CENTER, CHIEF, OFFICE OF RESEARCH, MARKETING & POLICY DEV, Washington, DC (US); JUNTENDO UNIVERSITY SCHOOL OF MEDICINE, DIVISION OF NEPHROLOGY, DEPARTMENT OF INTERNAL MEDICINE, Tokyo (JP); UNIVERSITY OF TENNESSEE RESEARCH FOUNDATION, Memphis, TN (US)

(72) Inventors: Hitoshi Suzuki, Hoover, AL (US); Run Fan, Omaha, NE (US); Bruce A. Julian, Birmingham, AL (US); Jan Novak, Pelham, AL (US); Zina Moldoveanu, Birmingham, AL (US); Zhixin Zhang, Omaha, NE (US); Milan Tomana, Birmingham, AL (US); Jiri Mestecky, Birmingham, AL (US); Robert J. Wyatt, Memphis, TN (US); Yasuhiko Tomino, Tokyo (JP); Yusuke Suzuki, Tokyo (JP); Stephen Olson, Rockville, MD (US); Matthew B. Renfrow, Birmingham, AL (US)

(73) Assignees: The UAB Research Foundation, Birmingham, AL (US); US Army Walter Reed Army Medical Center, Chief, Office Of Research, Marketing & Policy Dev Walter Reed Army Institute of Research, Washington, DC (US); Juntendo University School of Medicine, Division of Nephrology, Department of Internal Medicine, Tokyo (JP); University of Tennessee Research Foundation, Memphis, TN (US)

( * ) Notice: Subject to any disclaimer, the term of this patent is extended or adjusted under 35 U.S.C. 154(b) by 0 days.

(21) Appl. No.: 14/318,082

(22) Filed: Jun. 27, 2014

(65) Prior Publication Data

US 2014/0363436 A1 Dec. 11, 2014

Related U.S. Application Data

(62) Division of application No. 13/321,025, filed as application No. PCT/US2010/036239 on May 26, 2010, now abandoned.

(60) Provisional application No. 61/181,083, filed on May 26, 2009.

(51) Int. Cl.
A61K 39/395 (2006.01)
C07K 16/42 (2006.01)
G01N 33/68 (2006.01)

(52) U.S. Cl.
CPC .... *A61K 39/39541* (2013.01); *C07K 16/4283* (2013.01); *G01N 33/6854* (2013.01); *G01N 33/6893* (2013.01); *C07K 2317/41* (2013.01); *C07K 2317/55* (2013.01); *C07K 2317/565* (2013.01); *G01N 2800/347* (2013.01)

(58) Field of Classification Search
CPC .......... A61K 39/39566; C07K 16/4283; C07K 2317/30; C07K 2317/40; G01N 33/6854; G01N 33/6893; G01N 2800/347
USPC .................... 435/7.1; 436/63, 501, 507, 811; 530/387.1, 387.5
See application file for complete search history.

(56) References Cited

U.S. PATENT DOCUMENTS

2013/0224191 A1  8/2013  Stull et al.

OTHER PUBLICATIONS

Mestecky et al, Kidney Blood Press Res. 31:29-37, 2008; available online Jan. 8, 2008.*
Moldoveanu et al, Kidney Int. 71:1148-1154, 2007.*
Suzuki et al, J. Clin. Invest. 118(2):629-639, 2008.*
Tomana et al, Kidney Int. 52:509-516, 1997.*
Tomana et al, J. Clin. Invest. 104(1):73-81, 1999.*
Suzuki et al, J. Clin. Invest. 119(6):1668-1677, 2009.*
U.S. Appl. No. 13/321,025 , "Non Final Office Action", Oct. 9, 2013, 21 pages.
Allen et al., "Abnormal IgA glycosylation in Henoch-Schonlein purpura restricted to patients with clinical nephritis", Nephrol. Dial. Transplant. 13:930-4 (1998).
Allen et al., "Analysis of IgA1 O-glycans in IgA nephropathy by fluorophore-assisted carbohydrate electrophoresis", J. Am. Soc. Nephrol. 10:1763-71 (1999).
Allen et al., "Calactosylation of N- and O-linked carbohydrate moieties of IgA1 and IgG in IgA nephropathy", Clin. Exp. Immunol. 100:470-4 (1995).

(Continued)

*Primary Examiner* — Kevin Hill
(74) *Attorney, Agent, or Firm* — Kilpatrick Townsend & Stockton, LLP

(57) ABSTRACT

Provided are methods of diagnosing IgA nephropathy in a subject. Optionally, the methods comprise isolating an IgG from the subject and determining whether the IgG binds to a galactose-deficient IgA1. Optionally, the methods comprise providing a biological sample from the subject and detecting in the sample a mutation in a IGH gene, wherein the mutation is in a nucleotide sequence encoding a complementarity determining region 3 (CDR3) of a IGH variable region. Optionally, the methods comprise determining a level of IgG specific for a galactose-deficient IgA1 in the subject. Also provided are methods of treating or reducing the risk of developing IgA nephropathy in a subject.

7 Claims, 14 Drawing Sheets

(56) References Cited

OTHER PUBLICATIONS

Allen et al., "Leucocyte b1,3 galactosyltransferase activity in IgA nephropathy", Nephrol. Dial. Transplant. 12:701-6 (1997).
Allen et al., "Mesengial IgA1 in IgA nephropathy exhibits aberrant O-glycosylation: observations in three patients", Kidney Int. 60:969-73 (2001).
Amore et al., "Glycosylation of circulating IgA in patients with IgA nephropathy modulates proliferation and apoptosis of mesangial cells", J. Am. Soc. Nephrol. 12:1862-71 (2001).
Baenziger et al., "Structure of the carbohydrate units of IgA1 immunoglobulin II. Structure of the O-glycosidically linked oligosaccharide units", J. Biol. Chem. 249:7270-7281 (1974).
Barratt et al., "IgA nephropathy", J. Am. Soc. Nephrol. 16:2088-97 (2005).
Barratt et al., "The pathogenic role of IgA1 O-linked glycosylation in the pathogenesis of IgA nephropathy", Nephrology 12:275-84 (2007).
Barratt et al., "Immune complex formation in IgA nephropathy: a case of the 'right' antibodies in the 'wrong' place at the 'wrong' time?*", Nephrology Dialysis Transplantation 24.12 (2009): 3620-3623.
Bene et al., "Confirmation of tonsillar anomalies in IgA nephropathy: a multicenter study", Nephron 58:425-428 (1991).
Berger, "Recurrence of IgA nephropathy in renal allografts", Am. J. Kidney Dis. 12:371-372 (1988).
Berthoux et al., "Autoantibodies targeting galactose-deficient IgA1 associate with progression of IgA nephropathy", Journal of the American Society of Nephrology (2012): ASN-2012010053.
Buck et al., "B-cell O-galactosyltransferase activity, and expression of O-glycosylation genes in bone marrow in IgA nephropathy", Kidney Int. 73:1128-36 (2008).
*Caton et al., "Structural and functional implications of a restricted antibody response to a defined antigenic region on the influenza virus hemagglutinin", EMBO J. 5(7), 1986, pp. 1577-1587.
Conley et al., "Selective deposition of immunoglobulin A1 in immunoglobulin A nephropathy, anaphylactoid purpura nephritis, and systemic lupus erythematosus", J. Clin. Invest. 66:1432-6 (1980).
Coppo et al., "Aberrant glycosylation in IgA nephropathy", Kidney Int. 65:1544-7 (2004).
Coppo et al., "Characteristics of IgA and macromolecular IgA in sera from IgA nephropathy transplanted patients with and without IgAN recurrence", Contrib. Nephrol. 111:85-92 (1995).
Coppo et al., "Circulating immune complexes containing IgA, IgG and IgM in patients with primary IgA nephropathy and with Henoch-Schönlein nephritis. Correlation with clinical and histologic signs of activity", Clin. Nephrol. 18:230-9 (1982).
Coppo et al., "IgA nephropathy at two score and one", Kidney international 77.3 (2010): 181-186.
Coppo et al., "IgA serology in recurrent and non-recurrent IgA nephropathy after renal transplantation", Nephrol. Dial. Transplant. 10:2310-5 (1995).
Coppo et al., "IgA1 and IgA2 immune complexes in primary IgA nephropathy and Henoch-Schönlein nephritis", Clin. Exp. Immunol. 57:583-90 (1984).
Czerkinsky et al., "Circulating immune complexes and immunoglobulin A rheumatoid factor in patients with mesangial immunoglobulin A nephropathies", J. Clin. Invest. 77:1931-8 (1986).
D'Amico, "Natural history of idiopathic IgA nephropathy: role of clinical and histological prognostic factors", Am. J. Kidney Dis. 36:227-37 (2000).
*Dunn-Walters et al., "Characteristics of human IgA and IgM genes used by plasma cells in the salivary gland resemble those used in duodenum but not those used in the spleen" The Journal of Immunology 164.3 (2000): 1595-1601.
Emancipator et al., "Biology of disease. IgA nephropathy: Pathogenesis of the most common form of glomerulonephritis", Lab. Invest. 60:168-183 (1989).
Emancipator, "IgA nephropathy and Henoch-Schönlein syndrome", in Heptinstall's Pathology of the Kidney, Jennette et al. Editors, Lippincott-Raven Publishers: Philadelphia, p. 479-539 (1998).
Field et al., "O-linked oligosaccharides from human serum immunoglobulin A1", Biochem. Soc. Trans. 17:1034-5 (1989).
Floege et al., "Primary glomerulonephritis: A review of important recent discoveries", Kidney Research and Clinical Practice 32.3 (2013): 103-110.
Floege, "The pathogenesis of IgA nephropathy: what is new and how does it change therapeutic approaches?", American Journal of Kidney Diseases 58.6 (2011): 992-1004.
Gharavi et al., "Aberrant IgA1 glycosylation is inherited in familial and sporadic IgA nephropathy", Journal of the American Society of Nephrology 19.5 (2008): 1008-1014.
Glassock, "Analyzing antibody activity in IgA nephropathy", The Journal of clinical investigation 119.6 (2009): 1450-1452.
Glassock, "The pathogenesis of IgA nephropathy", Current opinion in nephrology and hypertension 20.2 (2011): 153-160.
Gonzales-Cabrero et al., "Characterization of circulating idiotypes containing immune complexes and their presence in the glomerular mesangium in patients with IgA nephropathy", Clin. Exp. Immunol. 76:204-9 (1989).
Greer et al., "The nucleotide sequence of the IgA1 hinge region in IgA nephropathy", Nephrol. Dial. Transplant. 13:1980-3 (1998).
*Griffiths et al., "Human anti-self antibodies with high specificity from phage display libraries", EMBO J. 12(2), 1993, pp. 725-734.
Hastings et al., "Biomarkers in IgA nephropathy: relationship to pathogenetic hits", Expert opinion on medical diagnostics 7.6 (2013): 615-627.
*Hawkins et al., GenBank Accession S44113, 1994.
*Hawkins et al., "Idiotypic Vaccination Against Human B-Cell Lymphoma. Rescue of Variable Region Gene Sequences From Biopsy Material for Assembly as Single-Chain Fv Personal Vaccines", Blood, vol. 83(11), Jun. 1994, pp. 3279-3288.
Hiki et al., "Mass spectrometry proves under-O-glycosylation of glomerular IgA1 in IgA nephropathy", Kidney Int. 59:1077-85 (2001).
Hiki et al., "O-linked oligosaccharide on IgA1 hinge region in IgA nephropathy. Fundamental study for precise structure and possible role", Contrib. Nephrol. 111:73-84 (1995).
Hiki et al., "Underglycosylation of IgA1 hinge plays a certain role for its glomerular deposition in IgA nephropathy", J. Am. Soc. Nephrol. 12:760-9 (1999).
Huang et al., "Somatic mutations modulate autoantibodies against galactose-deficient IgA1 in IgA nephropathy", Journal of the American Society of Nephrology (2016): ASN-2014101044.
Iwasaki et al., "Initiation of O-glycan synthesis in IgA1 hinge region is determined by a single enzyme, UDP-N-acetyl-a-D-galactosamine:polypeptide N-acetylgalactosaminyltransferase 2", J. Biol. Chem. 278:5613-21 (2003).
Jackson et al., "Aberrant synthesis of antibodies directed at the Fab of IgA in patients with IgA nephropathies", Clin. Immunol. Immunopath. 45:208-13 (1987).
Jennette, "The immunohistology of IgA nephropathy", Am. J. Kidney Dis. 12:348-52 (1988).
Ju et al., "A unique molecular chaperone Cosmc required for activity of the mammalian core 1 b3-galactosyltransferase", Proc. Natl. Acad. Sci. USA 99:16613-8 (2002).
Ju et al., "Cloning and expression of human core 1 b1,3-galactosyltransferase", J. Biol. Chem. 277:178-86 (2002).
Ju et al., "Protein glycosylation: chaperone mutation in Tn syndrome", Nature 437:1252 (2005).
Julian et al., "Allograft loss in IgA nephropathy", J. Am. Soc. Nephrol. 9:91A (1998).
Julian et al., "IgA nephropathy: an update", Current Opin. Nephrol. Hypertens. 13:171-9 (2004).
Kubagawa et al., "Precursor B cells transformed by Epstein-Barr virus undergo sterile plasma-cell differentiation: J-chain expression without immunoglobulin", Proc. Natl. Acad. Sci. USA 85:875-9 (1988).

(56) References Cited

OTHER PUBLICATIONS

Kudo et al., "Molecular cloning and characterization of a novel UDP-Gal:GalNAca peptide b1,3-galactosyltransferase (C1Gal-T2), an enzyme synthesizing a core 1 structure of O-glycan", J. Biol. Chem. 277:47724-31 (2002).
*Lee et al., "IgH Diversity in an Individual with Only One Million B Lymphocytes", Immunol. 3, 1993, pp. 211-222.
Levinsky et al., "IgA immune complexes in Henoch-Schönlein purpura", Lancet 2:1100-3 (1979).
Lomax-Smith et al., "IgA nephropathy—accumulated experience and current concepts", Pathology 17:219-24 (1985).
Matousovic et al., "IgA-1 containing immune complexes in the urine of IgA nephropathy patients", Nephrol. Dial. Transplant. 21:2478-84 (2006).
Mattu et al., "The glycosylation and structure of human serum IgA1, Fab, and Fc regions and the role of N-glycosylation on Fcα receptor interactions", J. Biol. Chem. 273:2260-72 (1998).
McCallum et al., "IgA nephropathy and thin basement membrane disease in association with Crohn disease", Pediat. Nephrol. 11:637-40 (1997).
Mestecky et al., "Comparative studies of the biological properties of human IgA subclasses", Protides Biol. Fluids 36:173-82 (1989).
Mestecky et al., "Defective galactosylation and clearance of IgA1 molecules as a possible etiopathogenic factor in IgA nephropathy", Contrib. Nephrol. 104:172-82 (1993).
Mestecky et al., "IgA nephropathy: current views of immune complex formation", Contrib. Nephrol. 157:56-63 (2007).
Mestecky, "Immunobiology of IgA", Am. J. Kidney Dis. 12:378-83 (1988).
*Minegishi et al., "Analysis of the CDR3 region of the rearranged IgH chain genes in patients with severe combined immunodeficiency and severe lymphopenia.", J. Immunol. 156, 1996, pp. 4666-4671.
Moore, "Reactivities of N-acetylgalactosamine-specific lectins with human IgA1 proteins", Mol. Immunol. 44:2598-604 (2007).
Moura et al., "Glycosylation and size of IgA1 are essential for interaction with mesangial transferring receptor in IgA nephropathy", J. Am. Soc. Nephrol. 15:622-34 (2004).
Nieuwhof et al., "Chronicity index and mesangial IgG deposition are risk factors for hypertension and renal failure in early IgA nephropathy", Am. J. Kidney Dis. 31:962-70 (1998).
Novak et al., "Analysis of aberrant O-glycosylation of IgA1 in patients with IgA nephropathy (IgAN)", American Society of Nephrology, 39th Renal Week Annual Meeting, San Diego, CA (2006).
Novak et al., "Heterogeneity of O-glycosylation in the hinge region of human IgA1", Mol. Immunol. 37:1047-56 (2000).
Novak et al., "IgA glycosylation and IgA immune complexes in the pathogenesis of IgA nephropathy", Semin. Nephrol. 28:78-87 (2008).
Novak et al., "IgA nephropathy and Henoch-Schoenien purpura nephritis: aberrant glycosylation of IgA1, formation of IgA1-containing immune complexes, and activation of mesangial cells", Contrib. Nephrol. 157:134-8 (2007).
Novak et al., "IgA1-containing immune complexes in IgA nephropathy differentially affect proliferation of mesangial cells", Kidney Int. 67:504-13 (2005).
Novak et al., "Interactions of human mesangial cells with IgA and IgA-containing immune complexes", Kidney Int. 62:465-75 (2002).
Novak et al., "Progress in molecular and genetic studies of IgA nephropathy", J. Clin. Immunol. 21:310-27 (2001).
Odum et al., "Recurrent mesangial IgA nephritis following renal transplantation", Nephrol. Dial. Transplant. 9:309-12 (1994).
Piller et al., "Biosynthesis of truncated O-glycans in the T cell line Jurkat. Localization of O-glycan initiation", J. Biol. Chem. 265:9264-71 (1990).
Qin et al., "Peripheral B lymphocyte beta1,3-galactosyltransferase and chaperone expression in immunoglobulin A nephropathy", J. Intern. Med. 258:467-77 (2005).
Raska et al., "Identification and characterization of CMP-NeuAc:GalNAc-IgA1 a2,6-sialyltransferase in IgA1-producing cells", J. Mol. Biol., 369:69-78 (2007).
Renfrow et al., "Determination of aberrant O-glycosylation in the IgA1 hinge region by electron capture dissociation Fourier transform-ion cyclotron resonance mass spectrometry", J. Biol. Chem. 280:19136-45 (2005).
*Rock et al., "CDR3 Length in Antigen-specific Immune Receptors", J. Exp. Med. 179, 1994, pp. 323-328.
Russell et al., "IgA-associated renal diseases: antibodies to environmental antigens in sera and deposition of immunoglobulins and antigens in glomeruli", J. Clin. Immunol. 6:74-86 (1986).
Rychlik et al., "The Czech registry of renal biopsies. Occurrence of renal diseases in the years 1994-2000", Nephrol. Dial. Transplant. 19:3040-9 (2004).
Sano et al., "Enzymatically deglycosylated human IgA1 molecules accumulate and induce inflammatory cell reaction in rat glomeruli", Nephrol. Dial. Transplant. 17:50-6 (2002).
Satake et al., "Kinetic analysis of glomerular deposition of IgA1 in a passive model of IgA nephropathy", IgAN Symposium 2009, Stresa, Italy, May 26-28, 2009.
Schachter et al., "Sialic acids. XIII. A uridine diphosphate D-galactose: mucin galactosyltransferase from porcine submaxillary gland", J. Biol. Chem. 246:5321-8 (1971).
Schena et al., "Increased serum levels of IgA1-IgG immune complexes and anti-F(ab')2 antibodies in patients with primary IgA nephropathy", Clin. Exp. Immunol. 77:15-20 (1989).
Sediva et al., "Binding sites for carrier-immobilized carbohydrates in the kidney: implication for the pathogenesis of Henoch-Schonlein purpura and/or IgA nephropathy", Nephrol. Dial. Transplant. 14:2885-91 (1999).
Silva et al., "Disappearance of glomerular mesangial IgA deposits after renal allograft transplantation", Transplantation 33:241-6 (1982).
Smith et al., "O-Glycosylation of serum IgD in IgA nephropathy", J. Am. Soc. Nephrol., 17:1192-9 (2006).
Sumiyama et al., "Adaptive evolution of the IgA hinge region in primates", Mol. Biol. Evol. 19:1093-9 (2002).
Suzuki et al., "Aberrantly glycosylated IgA1 in IgA nephropathy patients is recognized by IgG antibodies with restricted heterogeneity", J. Clin. Invest. 119:1668-77 (2009).
Suzuki et al., "Cloning and characterization of IgG antibodies specific to aberrantly glycosylated IgA1 in patients with IgA nephropathy", J. Am. Soc. Nephrol. 19:665A (Abstract) (2008).
Suzuki et al., "Epstein-Barr Virus-immortalized B Cells from Patients with IgA Nephropathy Secrete IgA1 with Galactose-deficient O-linked Glycans", 11th International Symposium on IgA Nephropathy, Oct. 5-7, 2006. Tokyo, Japan (2006).
Suzuki et al., "IgA1 nephropathy: characterization of IgG antibodies specific for galactose-deficient IgA1", Contrib. Nephrol. 157:129-33 (2007).
Suzuki et al., "The pathophysiology of IgA nephropathy", Journal of the American Society of Nephrology 22.10 (2011): 1795-1803.
Tarelli et al., "Human serum IgA1 is substituted with up to six O-glycans as shown by matrix assisted laser desorption ionization time-of-flight mass spectrometry", Carbohydr. Res. 339:2329-35 (2004).
Tiller et al., "Efficient generation of monoclonal antibodies from single human B cells by single cell RT-PCR and expression vector cloning", J. Immunol. Methods 329:112-24 (2008).
Tomana et al., "Receptor-mediated binding and uptake of immunoglobulin A by human liver", Gastroenterology 94:887-92 (1988).
Tomino et al., "Immunoglobulin A1 in IgA nephropathy", N. Engl. J. Med. 305:1159-60 (1981).
Van Den Wall Bake et al., "Shared idiotypes in mesangial deposits in IgA nephropathy are not disease-specific", Kidney Int. 44:65-74 (1993).
Van Der Boog et al., "Role of macromolecular IgA in IgA nephropathy", Kidney Int. 67:813-21 (2005).
Van Der Helm-Van Mil et al., "Immunoglobulin A multiple myeloma presenting with Henoch-Schönlein purpura associated with reduced sialylation of IgA1", Br. J. Haematol., 122:915-7 (2003).

(56) References Cited

OTHER PUBLICATIONS

Van Dixhoorn et al., "Combined glomerular deposition of polymeric rat IgA and IgG aggravates renal inflammation", Kidney Int. 58:90-9 (2000).
Wardermann et al., "Predominant autoantibody production by early human B cell precursors", Science 301:1374-7 (2003).
Xu et al., "Aberrantly glycosylated serum IgA1 are closely associated with pathologic phenotypes of IgA nephropathy", Kidney Int. 68:167-72 (2005).
Yanagawa et al., "A panel of serum biomarkers differentiates IgA nephropathy from other renal diseases", PloS one 9.5 (2014): e98081.
Yoshikawa et al., "Prognostic indicators in childhood IgA nephropathy", Nephron 60:60-7 (1992).
Zhao et al., "The level of galactose-deficient IgA1 in the sera of patients with IgA nephropathy is associated with disease progression", Kidney international 82.7 (2012): 790-796.
Zickerman et al., "IgA myeloma presenting as Henoch-Schönlein purpura with nephritis", Am. J. Kidney Dis. 36:E19 (2000).
Losman et al., "Relationships among antinuclear antibodies from autoimmune MRL mice reacting with histone H2A-H2B dimers and DNA," *Int. Immunol.* 5(5): 513-523 (1993).
Smith et al., "Complete amino acid sequences of the heavy and light chain variable regions from two A/J mouse antigen nonbinding monoclonal antibodies bearing the predominant p-azophenyl arsonate idiotype," *Biochemistry* 26: 604-612 (1993).

\* cited by examiner

Cells from IgAN patients

1123    YCSKVCRPWNYRRPYYYGMDVW

Mutation    A

Cells from healthy controls

9017    YCARVQRYDSTGYYPLGYLDLW

Mutation    S

SEQUENCE LISTING

```
<160> NUMBER OF SEQ ID NOS: 82

<210> SEQ ID NO 1
<211> LENGTH: 23
<212> TYPE: PRT
<213> ORGANISM: Homo sapiens

<400> SEQUENCE: 1

Tyr Cys Ser Arg Asp Leu Ala Ala Phe Cys Ser Gly Gly Asn Cys His
1               5                   10                  15

Ser Val Ala Ile Asp Phe Trp
            20
```

```
<210> SEQ ID NO 2
<211> LENGTH: 22
<212> TYPE: PRT
<213> ORGANISM: Homo sapiens

<400> SEQUENCE: 2

Tyr Cys Ser Lys Val Cys Arg Pro Trp Asn Tyr Arg Arg Pro Tyr Tyr
1               5                   10                  15

Tyr Gly Met Asp Val Trp
            20

<210> SEQ ID NO 3
<211> LENGTH: 17
<212> TYPE: PRT
<213> ORGANISM: Homo sapiens

<400> SEQUENCE: 3

Tyr Cys Ser Arg Asp Arg Tyr Tyr Cys Ser Gly Gly Ala Phe Asp Tyr
1               5                   10                  15

Trp

<210> SEQ ID NO 4
<211> LENGTH: 27
<212> TYPE: PRT
<213> ORGANISM: Homo sapiens

<400> SEQUENCE: 4

Tyr Cys Ser Arg Lys Thr Ser Tyr Pro Pro Thr Val Gly Glu Val Arg
1               5                   10                  15

Gly Thr Ser Tyr Tyr Tyr Gly Met Asp Val Trp
            20                  25

<210> SEQ ID NO 5
<211> LENGTH: 16
<212> TYPE: PRT
<213> ORGANISM: Homo sapiens

<400> SEQUENCE: 5

Tyr Cys Ser Lys Thr Lys Phe Lys Gly Tyr Ser Gly Phe His Tyr Trp
1               5                   10                  15

<210> SEQ ID NO 6
<211> LENGTH: 13
<212> TYPE: PRT
<213> ORGANISM: Homo sapiens

<400> SEQUENCE: 6

Tyr Cys Ser Arg Asp Arg Tyr Gly Leu Phe Asp Tyr Trp
1               5                   10

<210> SEQ ID NO 7
<211> LENGTH: 21
<212> TYPE: PRT
<213> ORGANISM: Homo sapiens

<400> SEQUENCE: 7

Tyr Cys Ala Thr Gly Asp Tyr Phe Gly Ser Gly Thr Tyr Pro Ile Gly
1               5                   10                  15

Ala Phe Asp Thr Trp
            20
```

```
<210> SEQ ID NO 8
<211> LENGTH: 9
<212> TYPE: PRT
<213> ORGANISM: Homo sapiens

<400> SEQUENCE: 8

Tyr Cys Ala Arg Asp Leu Asp Leu Trp
1               5

<210> SEQ ID NO 9
<211> LENGTH: 20
<212> TYPE: PRT
<213> ORGANISM: Homo sapiens

<400> SEQUENCE: 9

Tyr Cys Ala Ser Glu Gly His Leu Asp Tyr Gly Gly Asn Ser Asp Ala
1               5                   10                  15

Phe Asp Ile Trp
            20

<210> SEQ ID NO 10
<211> LENGTH: 18
<212> TYPE: PRT
<213> ORGANISM: Homo sapiens

<400> SEQUENCE: 10

Tyr Cys Ala Arg Asp Val Asn Ile Thr Ala Thr Glu Tyr Tyr Phe Asp
1               5                   10                  15

Tyr Trp

<210> SEQ ID NO 11
<211> LENGTH: 13
<212> TYPE: PRT
<213> ORGANISM: Homo sapiens

<400> SEQUENCE: 11

Tyr Cys Ala Arg Gly Asn Asp Asp Tyr Phe Asp Tyr Trp
1               5                   10

<210> SEQ ID NO 12
<211> LENGTH: 22
<212> TYPE: PRT
<213> ORGANISM: Homo sapiens

<400> SEQUENCE: 12

Tyr Cys Ala Arg Val Gln Arg Tyr Asp Ser Thr Gly Tyr Tyr Pro Leu
1               5                   10                  15

Gly Tyr Leu Asp Leu Trp
            20

<210> SEQ ID NO 13
<211> LENGTH: 20
<212> TYPE: PRT
<213> ORGANISM: Homo sapiens

<400> SEQUENCE: 13

Tyr Cys Ala Arg Glu Trp Tyr Ser Tyr Leu Trp Asp Ser Ser Tyr Tyr
1               5                   10                  15

Phe Asp Tyr Trp
            20
```

```
<210> SEQ ID NO 14
<211> LENGTH: 14
<212> TYPE: PRT
<213> ORGANISM: Homo sapiens

<400> SEQUENCE: 14

Cys Met Gln Gly Ile His Leu Pro Pro Thr Val Asp Val Phe
1               5                   10

<210> SEQ ID NO 15
<211> LENGTH: 12
<212> TYPE: PRT
<213> ORGANISM: Homo sapiens

<400> SEQUENCE: 15

Cys Cys Ser Tyr Ala Gly Ser Tyr Thr Ser Leu Phe
1               5                   10

<210> SEQ ID NO 16
<211> LENGTH: 12
<212> TYPE: PRT
<213> ORGANISM: Homo sapiens

<400> SEQUENCE: 16

Cys Ser Ser Tyr Val Gly Ser Asn Asn Ser Leu Phe
1               5                   10

<210> SEQ ID NO 17
<211> LENGTH: 14
<212> TYPE: PRT
<213> ORGANISM: Homo sapiens

<400> SEQUENCE: 17

Cys Gln Ser Tyr Asp Ser Ser Leu Ser Gly Tyr Val Val Phe
1               5                   10

<210> SEQ ID NO 18
<211> LENGTH: 11
<212> TYPE: PRT
<213> ORGANISM: Homo sapiens

<400> SEQUENCE: 18

Cys Gln Gln Tyr Asn Ser Tyr Pro Trp Thr Phe
1               5                   10

<210> SEQ ID NO 19
<211> LENGTH: 13
<212> TYPE: PRT
<213> ORGANISM: Homo sapiens

<400> SEQUENCE: 19

Cys Gln Gln Ala Asn Ser Phe Pro Pro Thr Gly Thr Phe
1               5                   10

<210> SEQ ID NO 20
<211> LENGTH: 11
<212> TYPE: PRT
<213> ORGANISM: Homo sapiens

<400> SEQUENCE: 20

Cys Gln Gln Ser Tyr Ser Thr Pro Arg Thr Phe
1               5                   10
```

```
<210> SEQ ID NO 21
<211> LENGTH: 18
<212> TYPE: PRT
<213> ORGANISM: Homo sapiens

<400> SEQUENCE: 21

Cys Lys Ala Trp Asp Asn Ser Leu Asn Ala His Thr Val Leu Gln Ala
1               5                   10                  15

Val Phe

<210> SEQ ID NO 22
<211> LENGTH: 11
<212> TYPE: PRT
<213> ORGANISM: Homo sapiens

<400> SEQUENCE: 22

Cys Gln Gln Tyr Asn Asn Trp Pro Gln Thr Phe
1               5                   10

<210> SEQ ID NO 23
<211> LENGTH: 11
<212> TYPE: PRT
<213> ORGANISM: Homo sapiens

<400> SEQUENCE: 23

Cys Gln Gln Ser Tyr Ser Thr Pro Pro Thr Phe
1               5                   10

<210> SEQ ID NO 24
<211> LENGTH: 11
<212> TYPE: PRT
<213> ORGANISM: Homo sapiens

<400> SEQUENCE: 24

Cys Gln Gln Tyr Gly Ser Ser Leu Tyr Thr Phe
1               5                   10

<210> SEQ ID NO 25
<211> LENGTH: 12
<212> TYPE: PRT
<213> ORGANISM: Homo sapiens

<400> SEQUENCE: 25

Cys Gln Val Trp Asp Ser Ser Ser Asp Val Val Phe
1               5                   10

<210> SEQ ID NO 26
<211> LENGTH: 12
<212> TYPE: PRT
<213> ORGANISM: Homo sapiens

<400> SEQUENCE: 26

Cys Gln Val Trp Asp Ser Ser Ser Asp His Pro Phe
1               5                   10

<210> SEQ ID NO 27
<211> LENGTH: 41
<212> TYPE: DNA
<213> ORGANISM: Artificial Sequence
<220> FEATURE:
<223> OTHER INFORMATION: Synthetic Construct

<400> SEQUENCE: 27
actgcaaccg gtgtacattc cgaggtgcag ctggtggagt c                41
```

<210> SEQ ID NO 28
<211> LENGTH: 33
<212> TYPE: DNA
<213> ORGANISM: Artificial Sequence
<220> FEATURE:
<223> OTHER INFORMATION: Synthetic Construct

<400> SEQUENCE: 28
atatattact gtgcgaaagt gtgtcgcccc tgg        33

<210> SEQ ID NO 29
<211> LENGTH: 36
<212> TYPE: DNA
<213> ORGANISM: Artificial Sequence
<220> FEATURE:
<223> OTHER INFORMATION: Synthetic Construct

<400> SEQUENCE: 29
aggggcgaca cactttcgca cagtaatata tggccg        36

<210> SEQ ID NO 30
<211> LENGTH: 35
<212> TYPE: DNA
<213> ORGANISM: Artificial Sequence
<220> FEATURE:
<223> OTHER INFORMATION: Synthetic Construct

<400> SEQUENCE: 30
ctgcgaagtc gacgctgaag agacggtgac cattg        35

<210> SEQ ID NO 31
<211> LENGTH: 41
<212> TYPE: DNA
<213> ORGANISM: Artificial Sequence
<220> FEATURE:
<223> OTHER INFORMATION: Synthetic Construct

<400> SEQUENCE: 31
tgtgtattac tgttccagag tccagcgcta tgatagcact g        41

<210> SEQ ID NO 32
<211> LENGTH: 40
<212> TYPE: DNA
<213> ORGANISM: Artificial Sequence
<220> FEATURE:
<223> OTHER INFORMATION: Synthetic Construct

<400> SEQUENCE: 32
atcatagcgc tggactctgg aacagtaata cacagccgtg        40

<210> SEQ ID NO 33
<211> LENGTH: 35
<212> TYPE: DNA
<213> ORGANISM: Artificial Sequence
<220> FEATURE:
<223> OTHER INFORMATION: Synthetic Construct

<400> SEQUENCE: 33
ctgcgaagtc gacgctgagg agacggtgac caggg        35

<210> SEQ ID NO 34
<211> LENGTH: 47
<212> TYPE: PRT
<213> ORGANISM: Homo sapiens

```
<400> SEQUENCE: 34

Cys His Val Lys His Tyr Thr Asn Pro Ser Gln Asp Val Thr Val Pro
1               5                   10                  15

Cys Pro Val Pro Ser Thr Pro Pro Thr Pro Ser Pro Ser Thr Pro Pro
                20                  25                  30

Thr Pro Ser Pro Ser Cys Cys His Pro Arg Leu Ser Leu His Arg
                35                  40                  45

<210> SEQ ID NO 35
<211> LENGTH: 22
<212> TYPE: PRT
<213> ORGANISM: Homo sapiens

<400> SEQUENCE: 35

Tyr Cys Ala Lys Val Cys Arg Pro Trp Asn Tyr Arg Arg Pro Tyr Tyr
1               5                   10                  15

Tyr Gly Met Asp Val Trp
                20

<210> SEQ ID NO 36
<211> LENGTH: 22
<212> TYPE: PRT
<213> ORGANISM: Homo sapiens

<400> SEQUENCE: 36

Tyr Cys Ser Arg Val Gln Arg Tyr Asp Ser Thr Gly Tyr Tyr Pro Leu
1               5                   10                  15

Gly Tyr Leu Asp Leu Trp
                20

<210> SEQ ID NO 37
<211> LENGTH: 4
<212> TYPE: PRT
<213> ORGANISM: Homo sapiens

<400> SEQUENCE: 37

Tyr Cys Ala Lys
1

<210> SEQ ID NO 38
<211> LENGTH: 10
<212> TYPE: PRT
<213> ORGANISM: Homo sapiens

<400> SEQUENCE: 38

Cys His Val Lys His Tyr Thr Asn Pro Ser
1               5                   10

<210> SEQ ID NO 39
<211> LENGTH: 10
<212> TYPE: PRT
<213> ORGANISM: Homo sapiens

<400> SEQUENCE: 39

Val Thr Val Pro Cys Pro Val Pro Ser Thr
1               5                   10

<210> SEQ ID NO 40
<211> LENGTH: 10
<212> TYPE: PRT
<213> ORGANISM: Homo sapiens
```

<400> SEQUENCE: 40

Ser Thr Pro Pro Thr Pro Ser Pro Ser Thr
1               5                   10

<210> SEQ ID NO 41
<211> LENGTH: 10
<212> TYPE: PRT
<213> ORGANISM: Homo sapiens

<400> SEQUENCE: 41

Thr Pro Pro Thr Pro Ser Pro Ser Cys Cys
1               5                   10

<210> SEQ ID NO 42
<211> LENGTH: 10
<212> TYPE: PRT
<213> ORGANISM: Homo sapiens

<400> SEQUENCE: 42

Val Pro Ser Thr Pro Pro Thr Pro Ser Pro
1               5                   10

<210> SEQ ID NO 43
<211> LENGTH: 20
<212> TYPE: PRT
<213> ORGANISM: Homo sapiens

<400> SEQUENCE: 43

Val Pro Ser Thr Pro Pro Thr Pro Ser Pro Ser Thr Pro Pro Thr Pro
1               5                   10                  15

Ser Pro Ser Cys
            20

<210> SEQ ID NO 44
<211> LENGTH: 4
<212> TYPE: PRT
<213> ORGANISM: Homo sapiens

<400> SEQUENCE: 44

Tyr Cys Ser Arg
1

<210> SEQ ID NO 45
<211> LENGTH: 4
<212> TYPE: PRT
<213> ORGANISM: Homo sapiens

<400> SEQUENCE: 45

Tyr Cys Ala Arg
1

<210> SEQ ID NO 46
<211> LENGTH: 4
<212> TYPE: PRT
<213> ORGANISM: Homo sapiens

<400> SEQUENCE: 46

Tyr Cys Ala Thr
1

<210> SEQ ID NO 47
<211> LENGTH: 4
<212> TYPE: PRT
<213> ORGANISM: Homo sapiens

<400> SEQUENCE: 47

Tyr Cys Ala Ser
1

<210> SEQ ID NO 48
<211> LENGTH: 4
<212> TYPE: PRT
<213> ORGANISM: Homo sapiens

<400> SEQUENCE: 48

Tyr Cys Ser Lys
1

<210> SEQ ID NO 49
<211> LENGTH: 64
<212> TYPE: DNA
<213> ORGANISM: Homo sapiens

<400> SEQUENCE: 49
tactgttcca gagatctggc cgcttttttgt agtggtggta actgccactc tgtggcgatt     60
gact                                                                  64

<210> SEQ ID NO 50
<211> LENGTH: 42
<212> TYPE: DNA
<213> ORGANISM: Homo sapiens

<400> SEQUENCE: 50
tgcatgcaag gtatacacct tcctcccaca gtggacgttt tc                        42

<210> SEQ ID NO 51
<211> LENGTH: 66
<212> TYPE: DNA
<213> ORGANISM: Homo sapiens

<400> SEQUENCE: 51
tactgttcca aagtgtgtcg cccctggaac tatagaaggc cctactatta cggaatggac     60
gtctgg                                                                66

<210> SEQ ID NO 52
<211> LENGTH: 36
<212> TYPE: DNA
<213> ORGANISM: Homo sapiens

<400> SEQUENCE: 52
tgctgctcat atgccggcag ctacacttcc ctcttc                                36

<210> SEQ ID NO 53
<211> LENGTH: 51
<212> TYPE: DNA
<213> ORGANISM: Homo sapiens

<400> SEQUENCE: 53
tactgttcca gagatcgtta ctattgtagt ggtggtgcct ttgactactg g               51

<210> SEQ ID NO 54
<211> LENGTH: 36
<212> TYPE: DNA
<213> ORGANISM: Homo sapiens

```
<400> SEQUENCE: 54
tgcagctcat atgtcggcag caacaattcc ctcttc                                 36

<210> SEQ ID NO 55
<211> LENGTH: 81
<212> TYPE: DNA
<213> ORGANISM: Homo sapiens

<400> SEQUENCE: 55
tactgttcca gaaagacctc ctacccccccc actgttgggg aggtaagagg gacctcctac      60
tattacggta tggacgtctg g                                                 81

<210> SEQ ID NO 56
<211> LENGTH: 42
<212> TYPE: DNA
<213> ORGANISM: Homo sapiens

<400> SEQUENCE: 56
tgccagtcct atgacagcag cctgagtggt tatgtggtat tc                          42

<210> SEQ ID NO 57
<211> LENGTH: 48
<212> TYPE: DNA
<213> ORGANISM: Homo sapiens

<400> SEQUENCE: 57
tactgttcaa aaccaagtt taagggatat agcggatttc attactgg                     48

<210> SEQ ID NO 58
<211> LENGTH: 33
<212> TYPE: DNA
<213> ORGANISM: Homo sapiens

<400> SEQUENCE: 58
tgccaacagt ataatagtta tccctggacg ttc                                    33

<210> SEQ ID NO 59
<211> LENGTH: 39
<212> TYPE: DNA
<213> ORGANISM: Homo sapiens

<400> SEQUENCE: 59
tactgttcca gagatcgcta cggcctattt gactactgg                              39

<210> SEQ ID NO 60
<211> LENGTH: 39
<212> TYPE: DNA
<213> ORGANISM: Homo sapiens

<400> SEQUENCE: 60
tgtcaacagg ctaacagttt ccctcccaca ggcacttttt                             39

<210> SEQ ID NO 61
<211> LENGTH: 63
<212> TYPE: DNA
<213> ORGANISM: Homo sapiens

<400> SEQUENCE: 61
tactgtgcaa ctgggggatta ctttggttcg gggacttacc ccatagggggc ttttgatacc     60 tgg                                                                     63
```

<210> SEQ ID NO 62
<211> LENGTH: 33
<212> TYPE: DNA
<213> ORGANISM: Homo sapiens

<400> SEQUENCE: 62
tgtcaacaga gttacagtac ccctcggacg ttc                           33

<210> SEQ ID NO 63
<211> LENGTH: 27
<212> TYPE: DNA
<213> ORGANISM: Homo sapiens

<400> SEQUENCE: 63
tactgtgcga gagatctcga tctctgg                                  27

<210> SEQ ID NO 64
<211> LENGTH: 33
<212> TYPE: DNA
<213> ORGANISM: Homo sapienst

<400> SEQUENCE: 64
tgtcagcagt ataataactg gcctcaaacg ttc                           33

<210> SEQ ID NO 65
<211> LENGTH: 60
<212> TYPE: DNA
<213> ORGANISM: Homo sapiens

<400> SEQUENCE: 65
tactgtgcga gcgagggaca tcttgactac ggtggtaact ccgatgcttt tgatatctgg    60

<210> SEQ ID NO 66
<211> LENGTH: 33
<212> TYPE: DNA
<213> ORGANISM: Homo sapiens

<400> SEQUENCE: 66
tgtcaacaga gttacagtac acctcccaca ttc                           33

<210> SEQ ID NO 67
<211> LENGTH: 54
<212> TYPE: DNA
<213> ORGANISM: Homo sapiens

<400> SEQUENCE: 67
tactgtgcga gagacgttaa tattacggcc actgagtact actttgacta ctgg      54

<210> SEQ ID NO 68
<211> LENGTH: 54
<212> TYPE: DNA
<213> ORGANISM: Homo sapiens

<400> SEQUENCE: 68
tgcaaagcat gggataacag cctgaatgct cacacagtgc tccaggcggt attc      54

<210> SEQ ID NO 69
<211> LENGTH: 39
<212> TYPE: DNA
<213> ORGANISM: Homo sapiens

<400> SEQUENCE: 69
tactgtgcga gagggaacga cgactacttt gactactgg                     39

```
<210> SEQ ID NO 70
<211> LENGTH: 33
<212> TYPE: DNA
<213> ORGANISM: Homo sapiens

<400> SEQUENCE: 70
tgtcagcagt atggtagctc actttacact ttt                          33

<210> SEQ ID NO 71
<211> LENGTH: 66
<212> TYPE: DNA
<213> ORGANISM: Homo sapiens

<400> SEQUENCE: 71
tactgtgcga gagtccagcg ctatgatagc actggttact accctctggg atacctcgat    60
ctctgg                                                               66

<210> SEQ ID NO 72
<211> LENGTH: 36
<212> TYPE: DNA
<213> ORGANISM: Homo sapiens

<400> SEQUENCE: 72
tgtcaggtgt gggacagcag tagtgatgtg gtattc                       36

<210> SEQ ID NO 73
<211> LENGTH: 60
<212> TYPE: DNA
<213> ORGANISM: Homo sapiens

<400> SEQUENCE: 73
tactgtgcga gagagtggta cagctatcta tgggactcgt cgtactactt tgactactgg    60

<210> SEQ ID NO 74
<211> LENGTH: 36
<212> TYPE: DNA
<213> ORGANISM: Homo sapiens

<400> SEQUENCE: 74
tgtcaggtgt gggacagtag tagtgatcat ccattc                       36

<210> SEQ ID NO 75
<211> LENGTH: 379
<212> TYPE: DNA
<213> ORGANISM: Homo sapiens

<400> SEQUENCE: 75
gaggtgcagc tggtggagtc tgggggaggc ttggtacagc ctgggggggtc cctgagactc    60 tcctgtgaag cctctggatt cacctttagc agctatgcca tggcctgggt ccgccaggct   120
ccagggaagg ggctggagtg ggtctcagct attagtggta gtggtggtag cacatactac   180
gcagactccg tgaaggggcg gttcaccatc tccagagaca attccaagaa caccctgtat   240
ctgcaaatga acagcctgag agccgaggac acggccatat attactgttc caaagtgtgt   300 cgccctgga actatagaag gccctactat tacggaatgg acgtctgggg ccaagggaca   360
atggtcaccg tctcctcag                                               379

<210> SEQ ID NO 76
<211> LENGTH: 331
<212> TYPE: DNA
<213> ORGANISM: Homo sapiens
```

<400> SEQUENCE: 76

```
cagtctgccc tgactcagcc tcgctcagtg tccgggtctc ctggacagtc agtcagcatc      60
tcctgcactg gaaccagcag tgatgttgga ggttataact atgtctcctg gtaccaacag     120
cacccaggca aagcccccaa actcatgatt tatgatgtca gtaagcggcc ctcaggggtc     180
cctgatcgct tctctggctc caagtctggc aacacggcct ccctgaccat ctctgggctc     240
caggctgagg atgaggctga ttattactgc tgctcatatg ccggcagcta cacttccctc     300
ttcggcggag ggaccaagct gaccgtccta g                                    331
```

<210> SEQ ID NO 77
<211> LENGTH: 379
<212> TYPE: DNA
<213> ORGANISM: Homo sapiens

<400> SEQUENCE: 77

```
gaggtgcagc tggtggagtc tgggggaggc ttggtccagc ctgggggtc cctgagactc       60
tcctgtgcag cctctggatt cacctttagt agctattgga tgagctgggt ccgccaggct     120
ccagggaagg gctgagtg gtggccaac ataaagcaag atggaagtga gaaatactat         180
gtggactctg tgaagggccg attcaccatc tccagagaca cgccaagaa ctcactgtat       240
ctgcaaatga acagcctgag agccgaggac acggctgtgt attactgtgc gagagtccag     300
cgctatgata gcactggtta ctaccctctg ggatacctcg atctctgggg ccgtggcacc     360
ctggtcaccg tctcctcag                                                   379
```

<210> SEQ ID NO 78
<211> LENGTH: 317
<212> TYPE: DNA
<213> ORGANISM: Homo sapiens

<400> SEQUENCE: 78

```
tatgagctga ctcagccact ctcagtgtca gtggccctgg gacagacggc caggattacc      60
tgtgggggaa acaacattgg aagtaaaaat gtgcactggt accagcagaa gccaggccag     120
gcccctgtgc tggtcatcta tagggatagc aaccggccct ctgggatccc tgagcgattc     180
tctggctcca actctgggaa cacggccacc ctgaccatca gcagagccca agccggggat     240
gaggccgact attactgtca ggtgtgggac agcagtagtg atgtggtatt cggcggaggg     300
accaagctga ccgtcct                                                    317
```

<210> SEQ ID NO 79
<211> LENGTH: 126
<212> TYPE: PRT
<213> ORGANISM: Homo sapiens

<400> SEQUENCE: 79

```
Glu Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Phe Ser Ser Tyr
            20                  25                  30

Ala Met Ala Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Ile Tyr Tyr Cys
                85                  90                  95

Ser Lys Val Cys Arg Pro Trp Asn Tyr Arg Arg Pro Tyr Tyr Tyr Gly
            100                 105                 110

Met Asp Val Trp Gly Gln Gly Thr Met Val Thr Val Ser Ser
            115                 120                 125

<210> SEQ ID NO 80
<211> LENGTH: 110
<212> TYPE: PRT
<213> ORGANISM: Homo sapiens

<400> SEQUENCE: 80

Gln Ser Ala Leu Thr Gln Pro Arg Ser Val Ser Gly Ser Pro Gly Gln
1               5                   10                  15

Ser Val Ser Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Tyr Thr Ser Leu Phe Gly Gly Gly Thr Lys Leu Thr Val Leu
            100                 105                 110

<210> SEQ ID NO 81
<211> LENGTH: 126
<212> TYPE: PRT
<213> ORGANISM: Homo sapiens

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gln Arg Tyr Asp Ser Thr Gly Tyr Tyr Pro Leu Gly Tyr
            100                 105                 110

Leu Asp Leu Trp Gly Arg Gly Thr Leu Val Thr Val Ser Ser
            115                 120                 125

<210> SEQ ID NO 82
<211> LENGTH: 105
<212> TYPE: PRT
<213> ORGANISM: Homo sapiens
```

```
<400> SEQUENCE: 82

Tyr Glu Leu Thr Gln Pro Leu Ser Val Ser Val Ala Leu Gly Gln Thr
1               5                   10                  15

Ala Arg Ile Thr Cys Gly Gly Asn Asn Ile Gly Ser Lys Asn Val His
            20                  25                  30

Trp Tyr Gln Gln Lys Pro Gly Gln Ala Pro Val Leu Val Ile Tyr Arg
        35                  40                  45

Asp Ser Asn Arg Pro Ser Gly Ile Pro Glu Arg Phe Ser Gly Ser Asn
    50                  55                  60

Ser Gly Asn Thr Ala Thr Leu Thr Ile Ser Arg Ala Gln Ala Gly Asp
65                  70                  75                  80

Glu Ala Asp Tyr Tyr Cys Gln Val Trp Asp Ser Ser Ser Asp Val Val
                85                  90                  95

Phe Gly Gly Gly Thr Lys Leu Thr Val
                100             105
```

DIAGNOSING AND TREATING IGA NEPHROPATHY

CROSS-REFERENCE TO RELATED APPLICATIONS

The present application is a divisional of U.S. application Ser. No. 13/321,025, filed on Jul. 3, 2012, which claims the benefit of U.S. Provisional Application No. 61/181,083, filed on May 26, 2009. The entire disclosure of each of the above-mentioned applications is hereby incorporated by reference herein in its entirety.

STATEMENT REGARDING FEDERALLY FUNDED RESEARCH

This invention was made with government funding under Grant Nos. 1 RO1 DK078244 and 1 PO1 DK61525 from the National Institutes of Health. The government has certain rights in this invention.

BACKGROUND

IgA nephropathy (IgAN), also called Berger disease, was described in 1968 based on the immunohistochemical finding of IgA- and IgG-containing immune complexes in the glomerular mesangium of the kidney. Proliferation of mesangial cells and expansion of the extracellular matrix can occur from the earliest stages of the disease, with progression to glomerular and interstitial sclerosis resulting in development of end-stage renal disease in 30%-40% of patients within 20 years of the estimated time of disease onset.

The IgA in the mesangial deposits is exclusively of the IgA1 subclass and is aberrantly glycosylated, with the hinge-region O-linked glycans being deficient in galactose (Gal). The IgA1 in the circulation of patients with IgAN also carries Gal-deficient O-glycans, although Gal-deficient variants are rarely found in the IgA1 in sera from normal individuals. The production of these variants is associated with altered expression of specific glycosyltransferases in the IgA1-producing cells. It is the binding of IgA1-containing immune complexes with aberrantly glycosylated IgA1 to mesangial cells that induces the renal manifestations characteristic of IgAN; however, the events that initiate the disease process are most likely of extra-renal origin, as IgAN recurs in more than 50% of patients within 2 years of kidney transplantation.

SUMMARY

Provided are methods of diagnosing IgA nephropathy in a subject. The methods include, for example, isolating an IgG from the subject and determining whether the IgG binds to a galactose-deficient IgA1. Binding of the IgG to the galactose-deficient IgA1 indicates the subject has or is at risk for developing IgA nephropathy.

The methods comprise providing a biological sample from the subject and detecting in the sample a mutation in a IGH gene, wherein the mutation is in a nucleotide sequence encoding a complementarity determining region 3 (CDR3) of a IGH variable region. A mutation in the nucleotide sequence compared to a control sequence indicates the subject has or is at risk for developing IgA nephropathy.

The methods comprise determining a level of IgG specific for a galactose-deficient IgA1 in the subject. An increase in the level of IgG specific for galactose-deficient IgA1 as compared to a control indicates the subject has or is at risk for developing IgA nephropathy. Optionally, the methods further comprise determining a level of galactose-deficient IgA1 in the subject. An increase in the level of galactose-deficient IgA1 as compared to a control indicates the subject has or is at risk for developing IgA nephropathy.

Also provided are methods of treating or reducing the risk of developing IgA nephropathy in a subject. The methods optionally comprise administering to the subject an agent, wherein the agent inhibits the binding of the IgG to galactose-deficient IgA1. The methods optionally comprise reducing a level of IgG specific for galactose-deficient IgA1 in a subject.

Also provided are isolated antibodies or fragments thereof. The isolated antibodies or fragments thereof are specific for a galactose-deficient hinge-region O-glycan of IgA1. The isolated antibodies can comprise an alanine to serine amino acid substitution in a complementarity determining region 3 (CDR3) of an IGH variable region.

Further provided are methods of detecting galactose-deficient IgA1 in a subject. The methods comprise obtaining a biological sample from the subject and utilizing an isolated antibody or fragment thereof specific for galactose-deficient IgA1 in an assay to detect galactose-deficient IgA1 in the subject.

Further provided is an isolated polypeptide comprising, consisting of, or consisting essentially of a galactose-deficient hinge-region O-glycan of IgA1.

Also provided are kits for performing immunoassays. The kits comprise a galactose-deficient IgA1, and a container. The kits can further comprise an IgG specific antibody. The kits can further comprise an assay substrate (e.g., a plate, a membrane, a well, etc.).

Also provided are methods of creating an animal model for IgA nephropathy. The methods comprise forming immune complexes in vitro, wherein the immune complexes comprise galactose-deficient IgA1 and IgG specific for galactose-deficient IgA1 and injecting the immune complexes into the animal. Injection of the immune complexes into the animal results in an animal model of IgA nephropathy. Further provided are animal models of IgA nephropathy comprising immune complexes with galactose-deficient IgA1 and IgG specific for galactose-deficient IgA1.

DESCRIPTION OF DRAWINGS

FIG. 1A shows an image of a Western blot demonstrating that Gal-deficient IgA1 (Mce) antigen bound serum IgG from 2 IgAN patients but serum IgG from 2 healthy controls minimally bound to the IgA1 heavy chain. After removal of sialic acid, IgG binding increased, as it did for binding to *Helix aspersa* agglutinin (HAA). N+, treated with neuraminidase; N−, not treated with neuraminidase. FIG. 1B shows an image of a Western blot demonstrating the glycan-specific binding of IgG. To test glycan-specific IgG binding to N-acetylgalactosamine (GalNAc) on IgA1, these IgA1 proteins were used: lane 1, Gal-deficient IgA1 (Mce); lane 2, desialylated and degalactosylated (dd)-IgA1; lane 3, enzymatically regalactosylated dd-IgA1; and lane 4, enzymatically resialylated dd-IgA1. dd-IgA1 bound the greatest amount of HAA, with enzymatically galactosylated or sialylated dd-IgA1 binding very little. IgG from an IgAN patient bound to these antigens in a fashion similar to that for HAA. FIG. 1C shows an image of a Western blot. Component chains of Gal-deficient IgA1 (Mce) were separated by SDS-PAGE under reducing conditions and electroblotted. The membrane was then treated with HAA to assess whether blockade with this GalNAc-specific lectin can inhibit IgG binding. FIG. 1D shows a bar graph demonstrating the intensity of each band as quantified by densitometry. The binding of serum IgG from an IgAN patient to Gal-deficient IgA1 was reduced by 66% after treatment with HAA. Conversely, blocking with serum IgG from an IgAN patient reduced the binding of HAA to Gal-deficient IgA1 by 60%. Binding of anti-human IgA (heavy-chain specific) confirmed equivalent loading. Representative results from 3 experiments are shown in A-C; lanes were run on the same gel but were noncontiguous.

FIGS. 2A and 2B shows graphs demonstrating that the levels of IgG directed against dd-IgA1 (2A) and Fab-IgA1 (2B) were higher in IgAN patients than in controls. Each group, n=16. P<0.0001; data are shown as individual values and mean±SD. FIG. 2C** shows a graph demonstrating IgG secreted by cell lines from IgAN patients and healthy controls (each group, n=10) was tested for binding to a hinge-region glycopeptide (HR-GalNAc-BSA) or HR-BSA, with or without HAA blockade. IgG produced by cell lines from IgAN patients bound to HR-GalNAc in an HAA-inhibitable fashion. *P<0.001; data are shown as the mean±SD. P values were generated using 2-tailed Student's t test. The experiments were repeated 3 times with similar results.

FIG. 3A shows a graph demonstrating size-exclusion chromatography and ELISA analysis of immune complexes formed in vitro with monomeric Gal-deficient IgA1 (50 μg) and monoclonal glycan-specific IgG (50 μg) from cell lines from 3 patients with IgAN (filled circles) or 3 healthy controls (open circles). IgG and monomeric (m) and dimeric (d) IgA1 standards were used to calibrate the column. Glycan-specific IgG from IgAN patients exhibited more binding to Gal-deficient IgA1 as compared with the binding of IgG from healthy controls. Immune complexes likely contained 1 or 2 molecules of IgA1 bound to 1 molecule of IgG. Data are shown as mean±SD. FIG. 3B shows an image of a Dot-blot analysis demonstrating that IgG secreted by cell lines from 5 of the 6 IgAN patients exhibited high binding to Gal-deficient IgA1; cell line no. 3081 from an IgAN patient and cells from 5 of the 6 healthy controls exhibited low binding. FIG. 3C shows a graph demonstrating that the findings shown in FIG. 3B were confirmed by densitometrical analysis. P<0.01; P values were generated using the 2-tailed Student's t test. Data are shown as individual values and mean±SD. Experiments were repeated 3 times with similar results.

FIG. 4A shows an image of a Western blot analysis using Gal-deficient IgA1 (Ale poly) as antigen that demonstrated binding of rIgG cloned from an IgAN patient (subject 1123) but only marginal binding of rIgG from a healthy control (subject 9017). FIG. 4B shows an image of a Western blot. The reduced Gal-deficient IgA1 (Mce1) (lane 1); enzymatically desialylated Gal-deficient IgA1 (Mce1) (lane 2); and desialylated and degalactosylated Gal-deficient IgA1 (Mce1) (lane 3) were incubated with rIgG after SDS-PAGE/Western blotting. Removal of sialic acid and Gal in the IgA1 hinge region increased the binding, suggesting that the rIgG bound specifically to GalNAc. FIG. 4C shows the amino acid (aa) sequence YCSKVCRPWNYRRPYYYGM-DVW (SEQ ID NO:2) in the CDR3 of VH of IgG from an IgAN patient (subject 1123) was reverted to the healthy control germline counterpart sequence YCAKVCRP-WNYRRPYYYGMDVW (SEQ ID NO:35) using an overlap PCR strategy. Conversely, the aa sequence YCARVQRYDSTGYYPLGYLDLW (SEQ ID NO:12) in the CDR3 of IgG from a healthy control (subject 9017) was mutated to generate YCSRVQRYDSTGYYPLGYLDLW (SEQ ID NO:36). FIG. 4D shows after the S to A substitution was introduced in CDR3 of VH of IgG of the cells from an IgAN patient (subject 1123), rIgG binding to Gal-deficient IgA1 was reduced by 72%. Conversely, the A to S substitution in CDR3 of IgG of the cells from a healthy control (subject 9017) increased binding to Gal-deficient IgA1. Anti-human IgA (heavy chain specific) Western blotting was used as load control. Results were evaluated densitometrically. Representative results from 2 experiments are shown in A-D; lanes were run on the same gel but were noncontiguous.

FIG. 5A shows an image of dot-blot assay. Gal-deficient IgA1 (Ale) placed in 96-well plates with PVDF membranes was incubated with normalized concentrations of serum IgG from IgAN patients, disease controls, and healthy controls; a representative example from 3 experiments is shown (20 samples from each group). The rIgG from an IgAN patient served as a positive control. Serum IgG from IgAN patients bound more to Gal-deficient IgA1 compared with the IgG from disease controls or healthy controls. FIG. 5B shows a scatter plot with the intensity of signal in each well measured by densitometry; the intensity of rIgG bound to Gal-deficient IgA was assigned a value of 100%. Serum IgG from IgAN patients has significantly higher reactivity to Gal-deficient IgA1 compared with that from healthy (P<0.0001) and disease controls (P<0.0001). Serum IgG from 54 of the 60 patients with IgAN showed values greater than the 90th percentile of the values for healthy controls. Wilcoxon's rank-sum test was used for 2-sample comparison. Data are shown as individual values and the mean±SD. FIG. 5C shows a graph showing ROC for serum IgG binding to Gal-deficient IgA1. The area under the curve is 0.9644. These data indicate a sensitivity of 88.3% and a specificity of 95.0% (P<0.0001; 95% CI, 0.928-1.00). The value of specificity is plotted as 1-specificity on the x axis. FIGS. 5D and 5E show scatter plots demonstrating the intensity of IgG binding to Gal-deficient IgA1 correlated with the UP/Cr ratio (5D) (P<0.0001) as well as with urinary IgA-IgG immune complexes (5E) (P=0.0082) in contemporaneously (i.e., within 30 days of renal biopsy) collected urine samples. UIgA-IgG IC/Cr, urinary excretion of IgA-IgG immune complexes/creatinine ratio.

FIG. 6A shows a graph demonstrating that immune complexes were formed from Gal-deficient IgA1 (Ale) and anti-glycan IgG in vitro. FIG. 6B shows a scanning electron microscopic image of a red blood cell in the urine of mice injected with the immune complexes. FIG. 6C shows microscopic images of the immune complexes (stained for human IgA, human IgG, and murine C3) deposited in the renal mesangium of the passive murine model of IgAN.

DETAILED DESCRIPTION

Figure 1A:
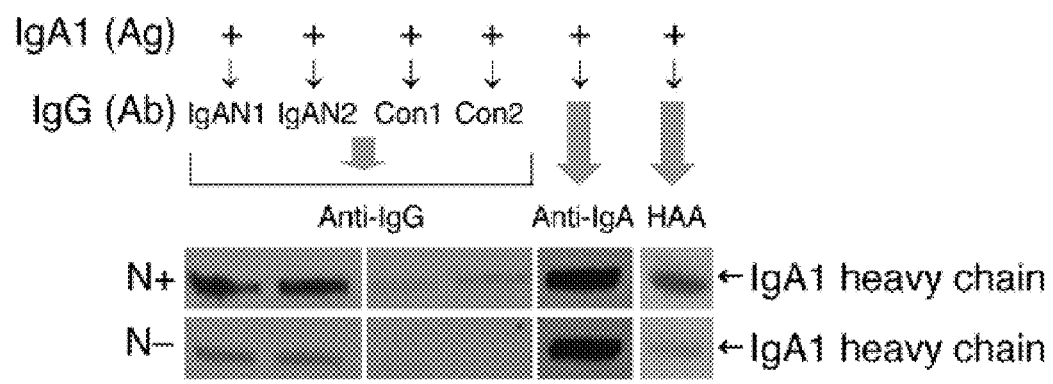
FIGS. 1A to 1D show serum IgG from IgA nephropathy (IgAN) patients exhibit specificity for GalNAc, binding to galactose-deficient and desialylated IgA1.

Provided herein are methods of diagnosing IgA nephropathy (IgAN) in a subject. The methods comprise isolating an IgG from the subject and determining whether the IgG binds to a galactose-deficient IgA1. Binding of the IgG to the galactose-deficient IgA1 indicates the subject has or is at risk of developing IgA nephropathy. The IgG can, for example, be isolated from a B cell. The B cell can be isolated from a population of peripheral blood mononuclear cells (PBMCs). Optionally, the B cell is immortalized. The B cell can, for example, be immortalized by transformation with an Epstein-Barr virus (EBV).

Optionally, determining binding of the IgG to the galactose-deficient IgA1 comprises performing an assay from the group consisting of a Western blot, an enzyme-linked immunosorbent assay (ELISA), an immunoaffinity assay, and a dot-blot assay.

Optionally, the method of diagnosing IgA nephropathy in a subject comprises providing a biological sample from the subject and detecting in the sample a mutation in an IGH gene, wherein the mutation is in a nucleotide sequence encoding a complementarity determining region 3 (CDR3) of an IGH variable region. A mutation in the nucleotide sequence compared to a control sequence indicates the subject has or is at risk of developing nephropathy. The mutation in the nucleotide sequence can be a somatic mutation (i.e., spontaneously occurring), or alternatively, the mutation can be a genetic mutation (i.e., passed down generationally from parents to offspring).

As used herein a biological sample is a sample derived from a subject and includes, but is not limited to, any cell, tissue or biological fluid. For example, the sample can be a tissue biopsy, blood or components thereof, bone marrow, urine, saliva, tissue infiltrate and the like. The biological fluid may be a cell culture medium or supernatant of cultured cells from a subject. Optionally, the biological sample contains cerebral spinal fluid.

Optionally, the biological sample comprises a genetic sample. The genetic sample comprises a nucleic acid, preferably RNA and/or DNA. A genetic sample may be obtained using any known technique including those described in Ausubel et al., Current Protocols in Molecular Biology (John Wiley & Sons, Inc., New York, 1999); Sambrook et al., Molecular Cloning: A Laboratory Manual, 3rd Ed., Cold Spring Harbor Laboratory Press, Cold Spring Harbor (2001); and Hames and Higgins, Nucleic Acid Hybridization (1984). The nucleic acid may be purified from whole cells using DNA or RNA purification techniques. The genetic sample may also be amplified using PCR or in vivo techniques requiring subcloning. The genetic sample can be obtained by isolating mRNA from the cells of the biological sample and reverse transcribing the RNA into DNA in order to create cDNA (Khan et al. Biochem. Biophys. Acta 1423: 17-28 (1999)).

The genetic sample can be analyzed for the presence or absence of a particular mutation. Thus, determining whether the CDR3 of the IGH variable region nucleotide sequence comprises a mutation can, for example, be carried out by a method selected from the list consisting of sequencing, PCR, RT-PCR, quantitative PCR, one step PCR, restriction fragment length polymorphism, hybridization techniques, Northern blot, microarray technology, gene chip, in situ hybridization, DNA microarray technology, and the like. Alternatively, determining whether the CDR3 of the IGH variable region amino acid sequence comprises a mutation can, for example, be carried out by Western Blot or protein sequencing. The analytical techniques to determine whether the CDR3 of the IGH variable region nucleotide sequence or amino acid sequences comprise a mutation are known. See, e.g., Sambrook et al., Molecular Cloning: A Laboratory Manual, 3rd Ed., Cold Spring Harbor Press, Cold Spring Harbor, N.Y. (2001).

As used throughout, the term mutation includes one or more deletions, insertions, or substitutions of one or more amino acids or nucleotides. Thus, in the provided methods, the mutation can be a deletion, insertion, or substitution. Optionally, the mutation is a deletion or substitution. By way of example, an insertion or deletion can result in an alteration of the reading frame of the gene, which alters the function of the gene. A point mutation or substitution can, for example, result in a mutation, e.g., a missense mutation, or a nonsense mutation, that alters the function of a gene. For example, the function of a gene can be altered in that the gene is no longer transcribed at wild-type levels. Alternatively, the amino acid sequence encoded by the gene no longer functions at control levels.

Optionally, the mutation in the IGH gene comprises one or more nucleotide substitutions resulting in an alanine to serine amino acid substitution in a YCAR (SEQ ID NO:45) or a YCAK (SEQ ID NO:37) amino acid sequence encoded by the IGH gene. Optionally, the nucleotide sequence encoding the CDR3 of the IGH variable region encodes an amino acid sequence comprising SEQ ID NO:1, SEQ ID NO:2, SEQ ID NO:3, SEQ ID NO:4, SEQ ID NO:5, or SEQ ID NO:6.

The method of diagnosing or characterizing IgA nephropathy in a subject optionally comprises determining a level of IgG specific for a galactose-deficient IgA1 in the subject. An increase in the level of IgG specific for galactose-deficient IgA1 as compared to a control indicates the subject has or is at risk of developing IgA nephropathy, or, if increased over a previous level, the same subject may indicate a progression in the IgA nepropathy and/or a need for a change in medication. Alternatively, if the level of IgG is compared to a subject with IgA nephropathy and the level is within the range of one or more subjects with IgA nephropathy, this indicates the subject has IgA nephropathy. Optionally, the method comprises determining a level of galactose-deficient IgA1 in the subject. An increase in the level of galactose-deficient IgA1 as compared to a control indicates the subject has or is at risk of developing IgA nephropathy, or, if increased over a previous level, the same subject may indicate a progression in the IgA nephropathy and/or a need for a change in medication. Alternatively, if the level of galactose-deficient IgA1 is compared to a subject with IgA nephropathy and the level is within the range of one or more subjects with IgA nephropathy, this indicates the subject has IgA nephropathy. A control can comprise a sample or known value from a subject or group of subjects that does not have IgA nephropathy. Alternatively, the control can comprise a sample or known value from the same subject prior to or early in the onset of IgA nephropathy.

Serum levels of galactose-deficient IgA1 are measured in reference to a standard galactose-deficient IgA1 myeloma protein. The amount of such protein that generates a certain OD value is defined as one unit. The result of measurement for IgA nephropathy patients, disease controls, and healthy controls are then compared, and depending on normality of distribution, a cut off value is defined, such as $90^{th}$ percentile of values for healthy controls. The results are further tested by receiver-operating characteristic (ROC)-curve analysis to define significance, sensitivity, and specificity at certain cut off values.

When performing an assay as described in Suzuki et al., J. Clin. Invest. 118:629-39 (2008), the standard galactose-deficient IgA1 myeloma protein is galactose-deficient IgA1 (Ale). The level of galactose-deficient IgA1 indicating a diagnosis of IgA nephropathy can, for example, be at least 95 units per milliliter (U/ml). Optionally, the level of galactose-deficient IgA1 indicating a diagnosis of IgA nephropathy can be in the range of about 95 U/ml to about 200 U/ml. Optionally, the level of galactose-deficient IgA1 can be about 110 U/ml to about 175 UNI. Optionally, the level of galactose-deficient IgA1 can be about 130 U/ml to about 155 U/ml.

When performing an assay as described in Moldoveanu et al., Kidney Int. 71:134-8 (2007), the standard galactose-deficient IgA1 myeloma protein is galactose deficient IgA1 (Mce). The level of galactose-deficient IgA1 indicating a diagnosis of IgA nephropathy can, for example, be at least 1000 units per milliliter (U/ml). Optionally, the level of galactose-deficient IgA1 indicating a diagnosis of IgA nephropathy can be in the range of about 1000 U/ml to about 8000 U/ml. Optionally, the level of galactose-deficient IgA1 can be about 1500 U/ml to about 4000 U/ml. Optionally, the level of galactose-deficient IgA1 can be about 1800 U/ml to about 2500 U/ml.

The level of IgG specific for galactose-deficient IgA1 can be measured, for example, by dot blot assay with galactose-deficient IgA1 (or its Fab fragment) as an antigen. Standard IgG (such as recombinant monoclonal IgG or standard polyclonal serum IgG) serve as a standard to calibrate measurement. The results of the measurement for IgA nephropathy patients, disease controls, and healthy controls are then compared, and depending on normality of distribution, a cut off value is defined, such as $90^{th}$ percentile of values for healthy controls. The results are further tested by receiver-operating characteristic (ROC)-curve analysis to define significance, sensitivity, and specificity at certain cut off values. For example, when dot-blot membranes were coated with galactose-deficient IgA1 (Ale) and a recombinant monoclonal IgG was used as the standard, the $90^{th}$ percentile for normal healthy controls was defined as about 17 units per 0.5 µg serum IgG (density of binding determined by densitometry and expressed as a percentage of binding of 0.5 µg of recombinant monoclonal IgG standard set to 100 units), thus 34 units per 1 mg serum IgG.

When performing an assay as described in Suzuki et al., J. Clin. Invest. 118:629-39 (2008), the serum level of IgG specific for a galactose-deficient IgA1 indicating a diagnosis of IgA nephropathy can, for example, be at least 35 units per 1 µg serum IgG (U/mg). Optionally, the serum level of IgG specific for galactose-deficient IgA1 indicating a diagnosis of IgA nephropathy can be in the range of about 35 U/µg to about 100 U/µg. Optionally, the serum level of IgG specific for galactose-deficient IgA1 can be about 50 U/µg to about 85 U/µg. Optionally, the serum level of IgG specific for galactose-deficient IgA1 can be about 60 U/µg to about 75 U/µg.

Optionally, the IgG or galactose-deficient IgA1 is isolated from the subject. The IgG or galactose-deficient IgA1 can, for example, be isolated from a B cell. Optionally, the B cell is isolated from a population of peripheral blood mononuclear cells (PBMCs). The B cell can be immortalized. Optionally, the B cell is immortalized by transformation with an Epstein-Barr virus.

Determining the level of IgG specific for galactose-deficient IgA1 or the level of galactose-deficient IgA1 comprises, for example, performing an assay from the group consisting of a Western blot, an enzyme-linked immunosorbent assay (ELISA), an immunoaffinity assay, and a dot-blot assay. However, other assay systems can be used.

Further provided are methods of treating or reducing the risk of developing IgA nephropathy in a subject. The method optionally comprises administering to the subject an agent, wherein the agent inhibits the binding of the IgG (and/or IgA1) to galactose-deficient IgA1. Inhibiting the binding of IgG and galactose-deficient IgA1 can comprise interfering with the formation of and/or reducing the size of the immune complexes formed by IgG and galactose-deficient IgA1 in subjects comprising IgA nephropathy. Optionally, the agent is selected from the group consisting of a small molecule, a polypeptide, an inhibitory nucleic acid molecule, a peptidomimetic, or a combination thereof. Optionally, the agent can be a polypeptide. The polypeptide can, for example, comprise the hinge region of IgA1 to be used as a competitive inhibitor to block binding of IgG with galactose-deficient IgA1. Optionally, the polypeptide can, for example, comprise a glycopeptide with a single GalNAc residue. The glycopeptide is recognized by the IgG specific for galactose-deficient IgA1, thus, preventing binding and the formation of immune complexes comprised of the IgG specific for galactose-deficient IgA1 and galactose-deficient IgA1. Optionally, the polypeptide can comprise an antibody. The antibody can be specific for the galactose-deficient hinge-region O-linked glycans of IgA1 to be used as a competitive inhibitor. Optionally, the antibody is a single-chain antibody (sc-Ab), a high affinity Fv antibody fragment, or a Fab antibody fragment specific for the hinge-region O-linked gylcans of IgA1.

The method of treating or reducing the risk of developing IgA nephropathy in a subject optionally comprises reducing a level of IgG specific for galactose-deficient IgA1 in the subject. Optionally, reducing the level of IgG specific for galactose-deficient IgA1 in the subject comprises the use of plasmapheresis. Optionally, reducing the level of IgG specific for galactose-deficient IgA1 in the subject comprises administering to the subject an agent that reduces the level of IgG in the subject. The agent can be selected from the group consisting of a small molecule, a polypeptide, an inhibitory nucleic acid molecule, a peptidomimetic, or a combination thereof. Optionally, an inhibitory nucleic acid molecule can be selected from the group consisting of a short interfering RNA (siRNA) molecule, a microRNA (miRNA) molecule, or an antisense nucleic acid molecule. The inhibitory nucleic acid molecule can, for example, target the gene encoding the IGH variable region of the IgG or the mRNA for the IGH variable region of the IgG in the subject to reduce the level of IgG specific for galactose-deficient IgA1.

Further provided are isolated antibodies or fragments thereof specific for a galactose-deficient hinge region O-linked glycans of IgA1. Optionally, the isolated antibody or fragment thereof comprises an alanine to serine amino acid substitution in the YCAR (SEQ ID NO:45) or a YCAK (SEQ ID NO:37) amino acid sequence encoded in the complementarity determining region 3 (CDR3) of an IGH variable region amino acid sequence. Optionally, the antibody comprises a monoclonal antibody. Also provided is a hybridoma cell line capable of producing the monoclonal antibody described herein. Optionally, the isolated antibodies or fragments thereof specific for the galactose-deficient hinge region O-linked glycans of IgA1 are produced by a cell line transfected with a vector encoding the antibody. The transfected cell line can, for example, comprise a primary cell line or an immortalized cell line. As defined herein, the term antibody includes, but is not limited to, fragments of the antibody, single-chain antibodies, conjugates of antibody fragments, chimeric antibodies, and hybrid antibodies.

Further provided herein are methods of detecting galactose-deficient IgA1 in a subject. The methods comprise obtaining a biological sample from the subject and utilizing an isolated antibody specific for galactose-deficient IgA1 to detect galactose-deficient IgA1 in the subject. An assay to detect galactose-deficient IgA1 in the subject can be selected from the group consisting of a Western blot, an enzyme-linked immunosorbent assay (ELISA), an immunoaffinity assay, an immunofluorescence assay, and a dot-blot assay. However, other assays can be used.

Also provided herein are isolated polypeptides comprising galactose-deficient hinge-region O-linked glycans of IgA1 or a fragment thereof. Optionally, the polypeptide consists of or consists essentially of the galactose-deficient hinge-region O-linked glycans of IgA1 or a fragment thereof The isolated polypeptide comprising the galactose-deficient hinge-region O-linked glycans of IgA1 can comprise the amino acid sequence CHVKHYTNPSQDVTVPCPVPST-PPTPSPSTPPTPSPSCCHPRLSLHR (SEQ ID NO:34). Fragments include, for example, CHVKHYTNPS (SEQ ID NO:38), VTVPCPVPST (SEQ ID NO:39), STPPTPSPST (SEQ ID NO:40), TPPTPSPSCC (SEQ ID NO:41), and VPSTPPTPSP (SEQ ID NO:42). Optionally, the fragment blocks binding of IgG specific for galactose-deficient IgA1 to galactose-deficient IgA1. Consequently, the polypeptide fragment thereof can be used as a competitive inhibitor of binding for IgG specific for galactose-deficient IgA1 binding to galactose-deficient IgA1.

Also provided are kits for performing immunoassays described herein. The kits comprise a galactose-deficient IgA1 and a container. Optionally, the kit further comprises an IgG specific antibody. The kit can further comprise an assay substrate (e.g., a plate, a membrane, and a well). Optionally, the kit can further comprise a control sample. The control sample can be from a patient with IgAN.

Optionally, the kit can comprise the isolated antibodies described herein and a container. The kit can further comprise an IgA1 specific antibody. Optionally, the kit can comprise as assay substrate. Optionally, the kit can further comprise a control sample. The control sample can comprise galactose-deficient IgA1.

Also provided are methods of creating an animal model of IgA nephropathy. The methods comprise forming immune complexes in vitro, wherein the immune complexes comprise galactose-deficient IgA1 and IgG specific for galactose-deficient IgA1 and injecting the immune complexes into the animal. Injection of the immune complexes into the animal results in an animal model of IgA nephropathy. Optionally, the animal model comprises a mouse model. Optionally, the mouse is a nude mouse. Optionally, the immune complexes are deposited in the renal mesangium of the animal model.

By nude mouse it is meant that the mouse contains mutations in both copies of the "nu" gene. The nude mouse does not contain a thymus, rendering the mouse incapable of producing T cells. Therefore, the nude mouse cannot reject tumors or transplants of cells from humans or other animals.

Also provided herein are animal models of IgA nephropathy comprising immune complexes with galactose-deficient IgA1 and IgG specific for galactose-deficient IgA1. Optionally, the animal model is produced by the methods disclosed herein. Optionally, the animal model is a mouse model.

As used herein, the term antibody encompasses whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively. Although antibodies are described throughout, fragments of antibodies, single-chain antibodies, conjugates of antibody fragments, chimeric antibodies, and hybrid antibodies can be used in the methods described herein.

The term variable is used herein to describe certain portions of the antibody domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies. The constant domains are not involved directly in binding an antibody to an antigen, but exhibit various effector functions, such as participation of the antibody in antibody-dependent cellular toxicity.

As used herein, the term epitope is meant to include any determinant capable of specific interaction with the provided antibodies. Epitopic determinants usually consist of chemically active surface groupings of molecules such as amino acids or sugar side chains and usually have specific three dimensional structural characteristics, as well as specific charge characteristics. Identification of the epitope that the antibody recognizes is performed as follows. First, various partial structures of the target molecule that the monoclonal antibody recognizes are prepared. The partial structures are prepared by preparing partial peptides of the molecule. Such peptides are prepared by, for example, known oligopeptide synthesis technique or by incorporating DNA encoding the desired partial polypeptide in a suitable expression plasmid. The expression plasmid is delivered to a suitable host, such as E. coli, to produce the peptides. For example, a series of polypeptides having appropriately reduced lengths, working from the C- or N-terminus of the target molecule, can be prepared by established genetic engineering techniques. By establishing which fragments react with the antibody, the epitope region is identified. The epitope is more closely identified by synthesizing a variety of smaller peptides or mutants of the peptides using established oligopeptide synthesis techniques. The smaller peptides are used, for example, in a competitive inhibition assay to determine whether a specific peptide interferes with binding of the antibody to the target molecule. If so, the peptide is the epitope to which the antibody binds. Commercially available kits, such as the SPOTs Kit (Genosys Biotechnologies, Inc.; The Woodlands, Tex.) and a series of multipin peptide synthesis kits based on the multipin synthesis method (Chiron Corporation, Emeryville, Calif.) may be used to obtain a large variety of oligopeptides.

The term antibody or fragments thereof can also encompass chimeric antibodies and hybrid antibodies, with dual or multiple antigen or epitope specificities, and fragments, such as F(ab')$_2$, Fab', Fab and the like, including hybrid fragments. Thus, fragments of the antibodies that retain the ability to bind their specific antigens are provided. For example, fragments of antibodies which maintain galactose-deficient IgA1 binding activity are included within the meaning of the term antibody or fragment thereof. Such antibodies and fragments can be made by techniques known in the art and can be screened for specificity and activity according to general methods for producing antibodies and screening antibodies for specificity and activity (See Harlow and Lane. Antibodies, A Laboratory Manual, Cold Spring Harbor Publications, New York (1988)).

Conjugates of antibody fragments and antigen binding proteins (single chain antibodies) can be used in the methods taught herein. Such conjugates of antigen binding proteins are described, for example, in U.S. Pat. No. 4,704,692, the contents of which are hereby incorporated by reference in their entirety.

Optionally, the antibody is a monoclonal antibody. The term monoclonal antibody as used herein refers to an antibody from a substantially homogeneous population of antibodies, i.e., the individual antibodies comprising the population are identical except for possible naturally occurring mutations that may be present in minor amounts. Monoclonal antibodies may be prepared using hybridoma methods, such as those described by Kohler and Milstein, Nature, 256:495 (1975) or Harlow and Lane, Antibodies, A Laboratory Manual, Cold Spring Harbor Publications, New York (1988). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro. The immunizing agent can be a galactose-deficient IgA1 or an immunogenic fragment thereof.

Generally, either peripheral blood lymphocytes (PBLs) are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, pp. 59-103 (1986)). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium") substances that prevent the growth of HGPRT-deficient cells.

Immortalized cell lines useful here are those that fuse efficiently, support stable high level expression of antibody by the selected antibody-producing cells, and are sensitive to a medium such as HAT medium. Immortalized cell lines include murine myeloma lines, which can be obtained, for instance, from the Salk Institute Cell Distribution Center; San Diego, Calif. and the American Type Culture Collection; Rockville, Md. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York (1987) pp. 51-63).

The culture medium in which the hybridoma cells are cultured can then be assayed for the presence of monoclonal antibodies directed against galactose-deficient IgA1 or selected epitopes thereof. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art, and are described further in Harlow and Lane Antibodies, A Laboratory Manual, Cold Spring Harbor Publications, New York (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells can serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody provided herein, or can be substituted for the variable domains of one antigen-combining site of an antibody to create a chimeric bivalent antibody comprising one antigen-combining site having specificity for galactose-deficient IgA1 and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')$_2$ fragment that has two antigen combining sites and is still capable of cross-linking antigen.

The Fab fragments produced in the antibody digestion can also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')$_2$ fragment is a bivalent fragment comprising two Fab' fragments linked by a disulfide bridge at the hinge region. Fab'-SH is the designation herein for Fab' in which the cysteine residue(s) of the constant domains bear a free thiol group.

One method of producing proteins comprising the provided antibodies or polypeptides is to link two or more peptides or polypeptides together by protein chemistry techniques. For example, peptides or polypeptides can be chemically synthesized using currently available laboratory equipment using either Fmoc (9-fluorenylmethyl-oxycarbonyl) or Boc (tert-butyloxycarbonoyl) chemistry (Applied Biosystems, Inc.; Foster City, Calif.). Those of skill in the art readily appreciate that a peptide or polypeptide corresponding to the antibody provided herein, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group that is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer Verlag Inc., NY). Alternatively, the peptide or polypeptide can by independently synthesized in vivo. Once isolated, these independent peptides or polypeptides may be linked to form an antibody or fragment thereof via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776 779 (1994)). The first step is the chemoselective reaction of an unprotected synthetic peptide a thioester with another unprotected peptide segment containing an amino terminal Cys residue to give a thioester linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini et al., FEBS Lett. 307:97-101 (1992); Clark et al., J. Biol. Chem. 269:16075 (1994); Clark et al., Biochemistry 30:3128 (1991); Rajarathnam et al., Biochemistry 33:6623-30 (1994)).

Alternatively, unprotected peptide segments can be chemically linked where the bond formed between the peptide segments as a result of the chemical ligation is an unnatural (non peptide) bond (Schnolzer et al., Science 256:221 (1992)). This technique has been used to synthesize analogs of protein domains as well as large amounts of relatively pure proteins with full biological activity (deLisle et al., Techniques in Protein Chemistry IV. Academic Press, New York, pp. 257-267 (1992)).

The provided polypeptide fragments can be recombinant proteins obtained by cloning nucleic acids encoding the polypeptide in an expression system capable of producing the polypeptide fragments thereof, such as a bacterial, adenovirus or baculovirus expression system. For example, one can determine the active domain of an antibody from a specific hybridoma that can cause a biological effect associated with the interaction of the antibody with galactose-deficient IgA1. For example, amino acids found to not contribute to either the activity or the binding specificity or affinity of the antibody can be deleted without a loss in the respective activity.

The provided fragments, whether attached to other sequences, can also include insertions, deletions, substitutions, or other selected modifications of particular regions or specific amino acids residues, provided the activity of the fragment is not significantly altered or impaired compared to the nonmodified antibody or epitope. These modifications can provide for some additional property, such as to remove or add amino acids capable of disulfide bonding, to increase its longevity, to alter its secretory characteristics, and the like. In any case, the fragment can possess a bioactive property, such as binding activity, regulation of binding at the binding domain, and the like. Functional or active regions may be identified by mutagenesis of a specific region of the protein, followed by expression and testing of the expressed polypeptide. Such methods can include site specific mutagenesis of the nucleic acid encoding the antigen. (Zoller et al., Nucl. Acids Res. 10:6487-500 (1982)).

Further provided herein is a humanized or human version of the antibody. Optionally, the antibody modulates the activity of the galactose-deficient IgA1 molecule by inhibiting binding of IgG to the galactose-deficient IgA1 molecule. Optionally, the humanized or human antibody comprises at least one complementarity determining region (CDR) of an antibody having the same epitope specificity as an antibody produced by the hybridoma cell line disclosed herein. For example, the antibody can comprise one or all CDRs of an antibody having the same epitope specificity as an antibody produced by the hybridoma cell line.

Optionally, the humanized or human antibody can comprise at least one residue of the framework region of the monoclonal antibody produced by a disclosed hybridoma cell line. Humanized and human antibodies can be made using methods known to a skilled artesian; for example, the human antibody can be produced using a germ-line mutant animal or by a phage display library.

Antibodies can also be generated in other species and humanized for administration to humans. Alternatively, fully human antibodies can also be made by immunizing a mouse or other species capable of making a fully human antibody (e.g., mice genetically modified to produce human antibodies) and screening clones that bind galactose-deficient IgA1. See, e.g., Lonberg and Huszar, Int. Rev. Immunol. 13:65-93, (1995), which is incorporated herein by reference in its entirety for methods of producing fully human antibodies. As used herein, the term humanized and human in relation to antibodies, relate to any antibody which is expected to elicit a therapeutically tolerable weak immunogenic response in a human subject. Thus, the terms include fully humanized or fully human as well as partially humanized or partially human.

Humanized forms of non-human (e.g., murine) antibodies or fragments thereof are chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. The humanized antibody optimally also will comprise at least a portion of an immunoglobulin constant region (Fc), typically that of a human immunoglobulin (Jones et al., Nature 321:522-525 (1986); Riechmann et al., Nature 332:323-327 (1988); and Presta, Curr. Op. Struct. Biol. 2:593-596 (1992)).

Generally, a humanized antibody has one or more amino acid residues introduced into it from a source that is non-human. These non-human amino acid residues are often referred to as import residues, which are typically taken from an import variable domain. Humanization can be essentially performed following the methods described in Jones et al., Nature 321:522-525 (1986); Riechmann et al., Nature 332:323-327 (1988); or Verhoeyen et al., Science 239:1534-1536 (1988), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The nucleotide sequences encoding the provided antibodies can be readily isolated and sequenced using conventional procedures (e.g., by using oligonucleotide probes that are capable of binding specifically to genes encoding the heavy and light chains of murine antibodies). These nucleotide sequences can also be modified, or humanized, for example, by substituting the coding sequence for human heavy and light chain constant domains in place of the homologous murine sequences (see, e.g., U.S. Pat. No. 4,816,567). The nucleotide sequences encoding any of the provided antibodies can be expressed in appropriate host cells. These include prokaryotic host cells including, but not limited to, *E. coli, Bacillus subtilus*, other enterobacteriaceae such as *Salmonella typhimurium* or *Serratia marcesans*, and various *Pseudomonas* species. Eukaryotic host cells can also be utilized. These include, but are not limited to, yeast cells (for example, *Saccharomyces cerevisiae* and *Pichia pastoris*), and mammalian cells such as VERO cells, HeLa cells, Chinese hamster ovary (CHO) cells, W138 cells, BHK cells, COS-7 cells, 293T cells and MDCK cells. The antibodies produced by these cells can be purified from the culture medium and assayed for binding, activity, specificity or any other property of the monoclonal antibodies by utilizing the methods set forth herein and standard in the art.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA 90:2551-255 (1993); Jakobovits et al., Nature 362:255-258 (1993); Bruggemann et al., Year in Immuno. 7:33 (1993)). Human antibodies can also be produced in phage display libraries (Hoogenboom et al., J. Mol. Biol. 227:381 (1991); Marks et al., J. Mol. Biol. 222:581 (1991)). The techniques of Cole et al. and Boerner et al. are also available for the preparation of human monoclonal antibodies (Cole et al., Monoclonal Antibodies and Cancer Therapy, Alan R. Liss, ed., p. 77 (1985); Boerner et al., J. Immunol. 147(1):86-95 (1991)).

Provided herein is an antibody, a humanized antibody, heavy and light chain immunoglobulins of an antibody, CDRs of the antibody, and certain truncations of these antibodies or immunoglobulins that perform the functions of the full length antibody or immunoglobulin. For example, the nucleic acid sequence coding for the antibodies can be altered. As such, nucleic acids that encode the polypeptide sequences, variants, and fragments of thereof are disclosed. These sequences include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequences.

As with all peptides, polypeptides, and proteins, including fragments thereof, it is understood that additional modifications in the amino acid sequence of the antibodies can occur that do not alter the nature or function of the peptides, polypeptides, or proteins. Such modifications include conservative amino acids substitutions and are discussed in greater detail below.

The isolated antibodies or fragments thereof provided herein have a desired function. The isolated antibody or fragment thereof binds a specific epitope of the galactose-deficient IgA1. Binding of the epitope can, for example, treat or reduce the risk of developing IgA nephropathy.

The antibodies described herein can be further modified and varied so long as the desired function is maintained. It is understood that one way to define any known modifications and derivatives or those that might arise, of the disclosed nucleic acid sequences and proteins herein is through defining the modifications and derivatives in terms of identity to specific known sequences. Specifically disclosed are polypeptides which have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the antibodies or fragments thereof provided herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman, Adv. Appl. Math 2:482 (1981), by the identity alignment algorithm of Needleman and Wunsch, J. Mol Biol. 48: 443 (1970), by the search for similarity method of Pearson and Lipman, Proc. Natl. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-7710 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Protein modifications include amino acid sequence modifications. Modifications in amino acid sequence may arise naturally as allelic variations (e.g., due to genetic polymorphism), may arise due to environmental influence (e.g., exposure to ultraviolet radiation), or may be produced by human intervention (e.g., by mutagenesis of cloned DNA sequences), such as induced point, deletion, insertion, and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. The mutations may or may not place the sequence out of reading frame and may or may not create complementary regions that could produce secondary mRNA structure. Substitutional modifications are those in which at least one residue has been removed and a different residue is inserted in its place. Conservative substitutions generally are made in accordance with the following Table 1.

TABLE 1

Amino Acid Substitutions

| Amino Acid | Substitutions (others are known in the art) |
| --- | --- |
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Non-conservative mutations can be made as well (e.g., proline for glycine).

Modifications, including the specific amino acid substitutions, are made by known methods. By way of example, modifications are made by site specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

As used herein, an inhibitory nucleic acid molecule can also be a short-interfering RNA (siRNA) molecule or a micro-RNA (miRNA) molecule. A 21-25 nucleotide siRNA or miRNA molecule can, for example, be produced from an expression vector by transcription of a short-hairpin RNA (shRNA) sequence, a 60-80 nucleotide precursor sequence, which is subsequently processed by the cellular RNAi machinery to produce either an siRNA or miRNA molecule. Alternatively, a 21-25 nucleotide siRNA or miRNA molecule can, for example, be synthesized chemically. Chemical synthesis of siRNA or miRNA molecules is commercially available from such corporations as Dharmacon, Inc. (Lafayette, Colo.), Qiagen (Valencia, Calif.), and Ambion (Austin, Tex.). A siRNA molecule preferably binds a unique sequence within the target mRNA with exact complementarity and results in the degradation of the target mRNA molecule. A siRNA molecule can bind anywhere within the target mRNA molecule. A miRNA molecule preferably binds a unique sequence within the target mRNA with exact or less than exact complementarity and results in the translational repression of the target mRNA molecule. A miRNA molecule can bind anywhere within the target mRNA sequence, but preferably binds within the 3' untranslated region of the target mRNA molecule. Methods of delivering siRNA or miRNA molecules are known in the art. See, e.g., Oh and Park, Adv. Drug. Deliv. Rev. 61(10):850-62 (2009); Gondi and Rao, J. Cell Physiol. 220(2):285-91 (2009); and Whitehead et al., Nat. Rev. Drug. Discov. 8(2):129-38 (2009).

As used herein, an inhibitory nucleic acid molecule can also be an antisense nucleic acid molecule. Antisense nucleic acid molecules can, for example, be transcribed from an expression vector to produce an RNA which is complementary to at least a unique portion of the target mRNA and/or the endogenous gene which encodes target mRNA. Hybridization of an antisense nucleic acid under specific cellular conditions results in inhibition of target protein expression by inhibiting transcription and/or translation.

Provided herein are methods of treating or reducing the risk of IgA nephropathy in a subject. Such methods include administering an effective amount of an agent comprising a small molecule, a polypeptide, an inhibitory nucleic acid molecule, a peptidomimetic or a combination thereof. Optionally, the small molecules, polypeptides, inhibitory nucleic acid molecules, and/or peptidomimetics are contained within a pharmaceutical composition.

Provided herein are compositions containing the provided small molecules, polypeptides, inhibitory nucleic acid molecules, and/or peptidomimetics and a pharmaceutically acceptable carrier described herein. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize degradation of the active ingredient and to minimize adverse side effects in the subject.

Suitable carriers and their formulations are described in *Remington: The Science and Practice of Pharmacy,* 21$^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the agent, e.g., the small molecule, polypeptide, inhibitory nucleic acid molecule, and/or peptidomimetic, to humans or other subjects.

The compositions are administered in a number of ways depending on whether local or systemic treatment is desired, and on the area to be treated. The compositions are administered via any of several routes of administration, including topically, orally, parenterally, intravenously, intraperitoneally, intramuscularly, subcutaneously, transdermally, or intrarenally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Optionally, the nucleic acid molecule or polypeptide is administered by a vector comprising the nucleic acid molecule or a nucleic acid sequence encoding the polypeptide. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based deliver systems. Such methods are well known in the art and readily adaptable for use with the compositions and methods described herein.

As used herein, plasmid or viral vectors are agents that transport the disclosed nucleic acids into the cell without degradation and include a promoter yielding expression of the nucleic acid molecule and/or polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., *Retroviruses*, Cold Spring Harbor Laboratory Press (1997), which is incorporated by reference herein for the vectors and methods of making them. The construction of replication-defective adenoviruses has been described (Berkner et al., J. Virol. 61:1213-20 (1987); Massie et al., Mol. Cell. Biol. 6:2872-83 (1986); Haj-Ahmad et al., J. Virol. 57:267-74 (1986); Davidson et al., J. Virol. 61:1226-39 (1987); Zhang et al., BioTechniques 15:868-72 (1993)). The benefit and the use of these viruses as vectors is that they are limited in the extent to which they can spread to other cell types, since they can replicate within an initial infected cell, but are unable to form new infections viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

The provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004).

The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003).

The provided polypeptides can be delivered by tegument aggregates. Methods for making and using tegument aggregates are described in International Publication No. WO 2006/110728.

Non-viral based delivery methods can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1α promoter, and the retroviral long terminal repeat (LTR).

The vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, subject can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g. IgA nephropathy). The term patient or subject includes human and veterinary subjects.

A subject at risk of developing a disease or disorder can be genetically predisposed to the disease or disorder, e.g., have a family history or have a mutation in a gene that causes the disease or disorder, or show early signs or symptoms of the disease or disorder. A subject currently with a disease or disorder has one or more than one symptom of the disease or disorder and may have been diagnosed with the disease or disorder.

The methods and agents as described herein are useful for both prophylactic and therapeutic treatment. For prophylactic use, a therapeutically effective amount of the agents described herein are administered to a subject prior to onset (e.g., before obvious signs of IgA nephropathy) or during early onset (e.g., upon initial signs and symptoms of IgA nephropathy). Prophylactic administration can occur for several days to years prior to the manifestation of symptoms of IgA nephropathy. Prophylactic administration can be used, for example, in the preventative treatment of subjects diagnosed with a genetic predisposition to IgA nephropathy. Therapeutic treatment involves administering to a subject a therapeutically effective amount of the agents described herein after diagnosis or development of IgA nephropathy.

According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to untreated levels. It is understood that treatment does not necessarily refer to a cure or complete ablation of the disease, condition, or symptoms of the disease or condition.

As used herein, the term reducing the risk of developing a disease or disorder refers to an action, for example, administration of a therapeutic agent, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to an untreated level. Such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

General Methods

Human Subjects.

Peripheral blood was collected from a total of 60 patients with biopsy-proven IgAN (IgA nephropathy) (mean age, 34.8±12.5 years; serum creatinine, 1.3±0.6 mg/dl; UP/Cr ratio, 1.31±1.60), from 40 healthy controls (mean age, 38.0±16.2 years; serum creatinine, 0.9±0.2 mg/dl; UP/Cr ratio, 0.06±0.06), and from 20 disease controls (patients with biopsy-proven lupus nephritis, membranous nephritis, and minimal change nephritic syndrome; mean age, 35.0±11.4 years; serum creatinine, 1.1±0.4 mg/dl; UP/Cr ratio, 1.56±1.93) (Table 2). The IgAN patients included 16 white males and 9 white females, 1 African-American male and 2 African-American females, and 12 Japanese males and 20 Japanese females. The healthy control group consisted of 12 white males and 12 white females, 2 African-American males and 4 African-American females, and 4 Japanese males and 6 Japanese females. All healthy controls had normal UP/Cr ratio or dipstick test for protein, and none exhibited microscopic hematuria. Disease controls consisted of a group of 5 white males and 1 white female and 1 African-American female, and 7 Japanese males and 6 Japanese females. The levels of IgA, Gal-deficient IgA1, and IgG in the serum samples from the 60 IgAN, 20 disease controls, and 40 healthy control subjects were determined by capture ELISA. For 20 of 60 patients with IgAN, urine and blood samples were collected within 30 days of renal biopsy (contemporaneous samples).

IgA, IgG, or IgM antibody (BioSource; Invitrogen). Avidin-horseradish peroxidase conjugate (ExtrAvidin; Sigma-Aldrich) and the peroxidase chromogenic substrate o-phenylenediamine-$H_2O_2$ (Sigma-Aldrich; St. Louis, Mo.) were then added. The color reaction was stopped with 1 M sulfuric acid, and the absorbance at 490 nm was measured using an EL312 BioKinetics Microplate Reader (BioTek; Winooski, Vt.). Standard curves for Igs were generated from a pool of normal human sera calibrated for all Ig isotypes (Binding Site; San Diego, Calif.). The results were calculated using a DeltaSoft III computer program (BioMetallics; Princeton, N.J.). Urinary IgA-IgG immune complexes were

TABLE 2

Clinical characteristics of study population.

|  | Cohort | Age | Male | Fem. | Race | Serum IgG (mg/ml) | Serum IgA (mg/ml) | SCr[a] (mg/dl) | UP/Cr[b] |
|---|---|---|---|---|---|---|---|---|---|
| IgAN | US 28 | 40.0 ± 15.2 | 17 | 11 | W25, B3 | 12.3 ± 2.7 | 4.4 ± 2.4 | 1.4 ± 0.9 | 1.2 ± 1.5 |
|  | Jap. 32 | 30.3 ± 7.0 | 12 | 20 | J32 | 12.1 ± 2.9 | 3.5 ± 1.1 | 1.2 ± 0.4 | 1.4 ± 1.7 |
|  | Tot. 60 | 34.8 ± 12.5 | 29 | 31 | W25, B3, J32 | 12.2 ± 2.8 | 3.9 ± 1.9 | 1.3 ± 0.6 | 1.3 ± 1.6 |
| Disease Cont. | US 7 | 33.7 ± 16.4 | 5 | 2 | W6, B1 | 17.2 ± 6.3 | 3.4 ± 1.2 | 1.0 ± 0.3 | 1.5 ± 2.6 |
|  | Jap. 13 | 35.7 ± 8.4 | 7 | 6 | J13 | 15.5 ± 3.5 | 3.8 ± 1.8 | 1.2 ± 0.4 | 1.6 ± 1.7 |
|  | Tot. 20 | 35.0 ± 11.4 | 12 | 8 | W6, B1, J13 | 16.1 ± 4.6 | 3.7 ± 1.6 | 1.1 ± 0.4 | 1.6 ± 1.9 |
| Healthy Cont. | US 30 | 38.6 ± 17.9 | 14 | 16 | W24, B6 | 10.4 ± 2.4 | 3.1 ± 1.7 | 1.0 ± 0.2 | 0.1 ± 0.1 |
|  | Jap. 10 | 36.1 ± 10.0 | 4 | 6 | J10 | 10.9 ± 2.9 | 2.8 ± 1.5 | 0.8 ± 0.2 | 0.1 ± 0.0 |
|  | Tot. 40 | 38.0 ± 16.2 | 18 | 22 | W24, B6, J10 | 10.5 ± 2.5 | 3.0 ± 1.7 | 0.9 ± 0.2 | 0.1 ± 0.1 |

Data expressed as mean ± SD. SCr[a] is serum creatinine concentration. UP/Cr[b] is urinary protein/creatinine ratio.

Isolation of PBMCs, Transformation with EBV, and Cloning of IgG-Secreting Cell Lines.

PBMCs from patients with IgAN and healthy controls were isolated from heparinized peripheral blood by Ficoll-Hypaque density gradient centrifugation. The B cell fraction was enriched from the PBMCs by removal of adherent cells through incubation in a plastic tissue-culture flask for 1 hour at 37° C. and removal of T cells by CD3 (PanT) Dynabeads, according to the manufacturer's instructions (Dynal; Invitrogen; Carlsbad, Calif.). PBMCs from 16 randomly selected IgAN patients (10 white males and 6 white females; 13 subjects had proteinuria or microscopic hematuria at the time of study) and 16 randomly selected white healthy controls (6 white males and 10 white females) were then immortalized with EBV (Suzuki et al., J. Clin. Invest. 118:629-39 (2008); Kubagawa et al., Proc. Natl. Acad. Sci. USA 85:875-9 (1988)). To establish cell lines from the initial EBV-immortalized PBMCs from patients with IgAN and healthy controls, IgG-secreting cells were subcloned by limiting dilution (using 96-well plates seeded with 5 to 10 cells per well) in RPMI 1640 supplemented with I-glutamine, 20% FCS, penicillin, and streptomycin (Suzuki et al., J. Clin. Invest. 118:629-39 (2008)). After several rounds of cloning and screening, IgG-producing cell lines were generated from all 16 IgAN patients and all 16 healthy controls.

Measurement of Ig and Immune-Complex Levels.

The isotypes of the Igs secreted by the immortalized cells were determined by capture ELISA (Tomana et al., J. Clin. Invest. 104:73-81 (1999); Moore et al., Mol. Immunol. 44:2598-604 (2007)). ELISA plates were coated with 1 g/ml of the F(ab')$_2$ fragment of goat IgG specific for human IgA, IgG, or IgM (Jackson ImmunoResearch Laboratories Inc.; West Grove, Pa.). The captured Igs were then detected with a biotin-labeled F(ab')$_2$ fragment of goat IgG anti-human measured using cross-capture ELISA (Matousovic et al., Nephrol. Dial. Transplant. 21:2478-84 (2006)).

Myeloma Proteins.

The IgA1 myeloma proteins that were isolated from plasma of patients with multiple myeloma are listed in Table 3 together with their molecular characteristics (Moore et al., Mol. Immunol. 44:2598-604 (2007)). In brief, plasma samples were precipitated with ammonium sulfate (50% saturation). The precipitate was then dissolved in and dialyzed against 10 mM sodium phosphate buffer (pH 7.0) prior to fractionation by ion-exchange chromatography on DEAE-cellulose, followed by affinity chromatography using Jacalin-agarose to capture IgA1 (Sigma-Aldrich) (Tomana et al., J. Clin. Invest. 104:73-81 (1999)). The final purification step was size-exclusion chromatography on columns of Sephadex G-200 or Ultrogel AcA 22 (Amersham Biosciences; Piscataway, N.J.). As the IgA myeloma proteins can be contaminated with IgG, the purified protein was subjected to affinity chromatography using staphylococcal protein G immobilized on agarose (Sigma-Aldrich). The purity of the IgA1 preparations was assessed by SDS-PAGE and Western blotting using an IgA1-specific monoclonal antibody (Tomana et al., J. Clin. Invest. 104:73-81 (1999)). The molecular form of the IgA1 proteins was assessed by size-exclusion chromatography, SDS-PAGE under non-reducing conditions, and Western blots developed with anti-IgA antibody.

TABLE 3

IgA1 myeloma proteins.

| Myeloma Protein | IgA isotype | Molecular Form |
|---|---|---|
| Mce | IgA1 | Polymer |
| Mce1 | IgA1 | Polymer |

TABLE 3-continued

IgA1 myeloma proteins.

| Myeloma Protein | IgA isotype | Molecular Form |
| --- | --- | --- |
| Ale mono | IgA1 | Monomer |
| Ale poly | IgA1 | Polymer |
| Fab-IgA1 | IgA1 | Fab frag. of IgA1cont. part of the hinge region |

ELISA Characterization of Antigen-Specific IgG Antibodies.

The binding of serum IgG from IgAN patients and healthy controls, as well as IgG secreted by EBV-immortalized cells from the same subjects, was analyzed by ELISA using a panel of antigens: dd-IgA1, Fab-IgA1 generated using an IgA-specific protease from *Haemophilus influenzae* HK50, HR-BSA, and HRGalNAc-BSA. HR-GalNAc was synthesized by Bachem (asterisks mark the sites with GalNAc): V-P-S-T-P-P-*T-P-*S-P-*S-T-P-P-T-P-S-P-S-C-NH$_2$ (SEQ ID NO:43). The hinge-region peptide was the same peptide but with no GalNAc. Both preparations were cross-linked to BSA.

For ELISA, flat-bottom 96-well plates (Nunc MaxiSorp; eBioscience; San Diego, Calif.) were coated with 1 µg/ml solution of the above-mentioned antigens. Serum or culture supernatant samples diluted in PBS were added to each well. The amount of total IgG used for the analyses was normalized in all samples. The captured IgG were detected with a biotin-labeled F(ab')$_2$ fragment of goat IgG anti-human IgG antibody (BioSource; Invitrogen). Avidin-horseradish peroxidase conjugate (ExtrAvidin; Sigma-Aldrich) was then added, and the reaction was developed as described before (Suzuki et al., J. Clin. Invest. 118:629-39 (2008)).

SDS-PAGE and Western Blotting.

Serum and culture supernatants were separated by SDS-PAGE under reducing conditions using 4%-20% gradient slab gels (Bio-Rad). The amounts of protein loaded were adjusted to achieve equivalent amounts of IgA protein in each lane. The gels were blotted onto PVDF membranes and incubated with antibody specific for IgA heavy chains (Vector Laboratories; Burlingame, Calif.) or a biotin-labeled lectin from *Helix aspersa* (HAA). HAA reacts with terminal GalNAc but not with sialylated GalNAc or GalNAc-Gal disaccharide. Gal-deficient IgA1 myeloma proteins (Mce or Ale poly), after separation by SDS-PAGE under reducing conditions and electroblotting onto PVDF membranes, served as antigens for analysis of glycan-specific IgG. The bound IgG was detected with IgG-specific antibody, and the visualization of positive bands was accomplished by subsequent incubation of the membrane with avidin-peroxidase conjugate, followed by enhanced chemiluminescence detection (Pierce; Thermo Scientific; Rockford, Ill.) (Suzuki et al., Contrib. Nephrol. 157:129-33 (2007); Moore et al., Mol. Immunol. 44:2598-604 (2007); Moldoveanu et al., Kidney Int. 71:1148-54 (2007)).

*Helix aspersa* Agglutinin (HAA) Inhibition.

To inhibit IgG binding to Gal-deficient IgA1 (Mce) myeloma protein or HR-GalNAc-BSA, 20 mg/ml unlabeled HAA was applied to PVDF membrane after electroblotting of IgA1 or to the wells of ELISA plates after coating with IgA1 protein.

Immune-Complex Formation In Vitro.

IgG was isolated from cell-culture supernatants of the IgG-secreting cell lines derived from patients with IgAN and healthy controls by protein G affinity chromatography (GE Healthcare; Piscataway, N.J.). These cell lines were subcloned by limiting dilution, and clones secreting glycan-specific IgG (binding to Gal-deficient IgA1) were selected. Immune complexes were formed in vitro by mixing 50 µg Gal-deficient IgA1 (Ale mono) and 50 µg purified glycan-specific IgG and incubating the mixture overnight at 4° C. The formed complexes were fractionated by HPLC on a calibrated TSK 3000 column (Tosoh Bioscience; South San Fransisco, Calif.), and 0.25 ml fractions were analyzed for IgA1-IgG immune complexes using cross-capture ELISA (Novak et al, Kidney Int. 62:465-75 (2002)).

Cloning of IGH, IGκ, and IGλ, Genes.

Single-cell reverse-transcription PCR was used to amplify the V(D)J regions for IGH, IGκ, and IGλ genes (Wardemann et al., Science 301:1374-7 (2003)). Reverse transcription and first-round PCR were performed with OneStep RT-PCR Kit (QIAGEN; Valencia, Calif.) under these conditions: 50° C., 30 minutes; 94° C., 15 minutes; 94° C., 20 seconds; 55° C., 30 seconds; 72° C., 1 minute for 50 cycles; 72° C., 10 minutes; and stop at 4° C. Second-round PCR was performed with rTaq DNA Polymerase (Invitrogen) under these conditions: 94° C., 3 minutes; 94° C., 20 seconds; 57° C. (IgH/Igκ) or 60° C. (Igλ), 30 seconds; 72° C., 45 seconds for 50 cycles; 72° C., 5 minutes; and stop at 4° C. One microliter of cDNA from first-round PCR was used as the template for the second-round PCR. The average single-cell RT-PCR efficiency was 38.4%. Positive PCR products were purified (QIAquick; QIAGEN) and sequenced. The resultant Ig gene sequences were analyzed with the IgBLAST program to determine the potential VH, DH, and JH germline gene usage and mutation analysis. The IgBLAST program is available on the internet through the National Center for Biotechnology Information. Restriction enzyme digestion sites were introduced in the second round of single-cell RT-PCR. Digested IgH, Igκ, and Igλ PCR products were purified using QIAquick PCR purification kit (QIAGEN) and directly cloned into specific expression vectors containing human Ig 1, Ig, or Ig constant regions. Plasmids were sequenced to confirm clones with inserts identical to that of the original PCR products. The pI values and CDR3 junction analysis were determined by IMGT/V-QUEST. The corresponding DNA sequences were deposited to GenBank (accession numbers FJ746335-FJ746360).

VH CDR3 Site-Specific Mutagenesis.

Site-directed mutagenesis was performed by 2-step PCR to generate amplicons with mutated (IgAN patient 1123) or unmutated (healthy control 9017) VH genes (Tiller et al., J. Immunol. Methods 329:112-24 (2008)). Primers used in PCR reverted the substitution (S to A) in the IgAN clone or mutated (A to S) the sequence in the clone from the healthy control (Table 4). The first PCR (PCR1) forward primer was VH specific and contained an AgeI restriction site. The PCR2 reverse primer was JH specific and contained the SalI restriction site. PCR products 1 and 2 were hybridized via the homologous region in the subsequent overlap PCR using the same 5'-AgeI VH-specific forward primer and the 3'-SalI JH-specific reverse primer and generated the complete VDJ sequence with desired mutations. Corresponding clones were sequenced and cloned into the IgG expression vector for production of rIgG.

TABLE 4

Primer sequences for mutatgenesis.

| Pat. #1123 | Sense | Sequence |
|---|---|---|
| PCR1 | Age1-VH3 | ACTGCAACCGGTGTACATTCCGAGGTGCAGCTGGTGGAGTC (SEQ ID NO: 27) |
| PCR2 | F-mutated | ATATATTACTGTGCGAAAGTGTGTCGCCCCTGG (SEQ ID NO: 28) |
| Overlap PCR | Age1-VH3 | ACTGCAACCGGTGTACATTCCGAGGTGCAGCTGGTGGAGTC (SEQ ID NO: 27) |

| Pat. #1123 | Antisense | Sequence |
|---|---|---|
| PCR1 | R-mutated | AGGGGCGACACACTTTCGCACAGTAATATATGGCCG (SEQ ID NO: 29) |
| PCR2 | Sal1-JH3 | CTGCGAAGTCGACGCTGAAGAGACGGTGACCATTG (SEQ ID NO: 30) |
| Overlap PCR | Sal1-JH3 | CTGCGAAGTCGACGCTGAAGAGACGGTGACCATTG (SEQ ID NO: 30) |

| Pat. #9017 | Sense | Sequence |
|---|---|---|
| PCR1 | Age1-VH3 | ACTGCAACCGGTGTACATTCCGAGGTGCAGCTGGTGGAGTC (SEQ ID NO: 27) |
| PCR2 | F-mutated | TGTGTATTACTGTTCCAGAGTCCAGCGCTATGATAGCACTG (SEQ ID NO: 31) |
| Overlap PCR | Age1-VH3 | ACTGCAACCGGTGTACATTCCGAGGTGCAGCTGGTGGAGTC (SEQ ID NO: 27) |

| Pat. #9017 | Antisense | Sequence |
|---|---|---|
| PCR1 | R-mutated | ATCATAGCGCTGGACTCTGGAACAGTAATACACAGCCGTG (SEQ ID NO: 32) |
| PCR2 | Sal1-JH145 | CTGCGAAGTCGACGCTGAGGAGACGGTGACCAGGG (SEQ ID NO: 33) |
| Overlap PCR | Sal1-JH145 | CTGCGAAGTCGACGCTGAGGAGACGGTGACCAGGG (SEQ ID NO: 33) | rIgG Antibody Production.

Human embryonic kidney cells (293H) were cultured in DMEM supplemented with 10% FBS (Ultra Low Bovine Ig content; Gibco, Invitrogen) and cotransfected with 10 µg plasmid DNA constructs encoding IgH and IgL chains by polyethyleneimine (Sigma-Aldrich) precipitation. After 16-hour transfection, the cell-culture medium was replaced with fresh medium. Supernatants with secreted IgG were collected after 7 days.

Fab Purification of rIgG.

The Fab fragment of rIgG from an IgAN patient was purified using the Pierce Fab Preparation Kit (Thermo Scientific).

Dot-Blot Analysis.

Gal-deficient IgA1 (Ale poly; 0.5 µg per well) was placed into the wells of a 96-well plate with PVDF membrane (MultiScreenHTS IP Filer Plate; Millipore) and blocked with SuperBlock (Pierce; Thermo Scientific). Serum or cell-culture supernatants (normalized to 0.5 µg IgG in each sample) were added and incubated overnight at 4° C. As a positive control, 0.5 µg of rIgG from an IgAN patient was used. The binding was detected with biotin-labeled IgG-specific antibody, followed by subsequent incubation of the membrane with avidin-peroxidase conjugate, and the reaction was visualized using enhanced chemiluminescence (Pierce; Thermo Scientific), as described above for Western blotting. Results were evaluated densitometrically. The intensity of rIgG binding to Gal-deficient IgA was assigned a value of 100%.

Statistics.

Correlations between different parameters were analyzed by 2-tailed Student's t test or by regression analysis. ANOVA was used to determine differences in the characteristics among multiple groups. Nonparametric methods, such as Spearman's rank correlation and Wilcoxon's rank-sum test were used for the correlation and 2-sample comparisons, respectively. Data were expressed as mean±SD or median values. P<0.05 was considered significant. These statistical analyses were performed with StatView 5.0 software (Abacus Concepts; Cheltenham, Gloucestershire, United Kingdom). The ROC for Gal-deficient IgA1-specific IgG levels in patients and controls was constructed using GraphPad Prism, version 4.00 for Windows (GraphPad Software; La Jolla, Calif.).

Results

Example 1

Serum IgG from IgAN Patients Exhibits Specificity for N-Acetylgalactosamine, which Results in Binding with Gal-Deficient and Desialylated IgA1

Binding of serum IgG from IgAN patients to Gal-deficient IgA1 was first determined using an ELISA in which the coated antigen was either enzymatically desialylated and degalactosylated IgA1 (dd-IgA1) or the Fab fragment of Gal-deficient IgA1 containing the N-terminal part of the hinge region with O-glycans attached (Fab-IgA1) (Table 3). The levels of serum IgG directed against dd-IgA1 and Fab-IgA1 were higher in IgAN patients than in healthy controls (P<0.001) (Table 5). These results, obtained using samples from 16 patients and 16 healthy controls from the southeastern USA, were corroborated using serum samples from 20 IgAN patients and 20 healthy controls from Japan (P<0.0001) (Table 5).

Figure 1B:
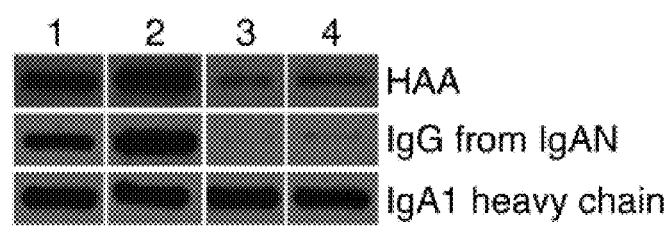
Figure 1C:
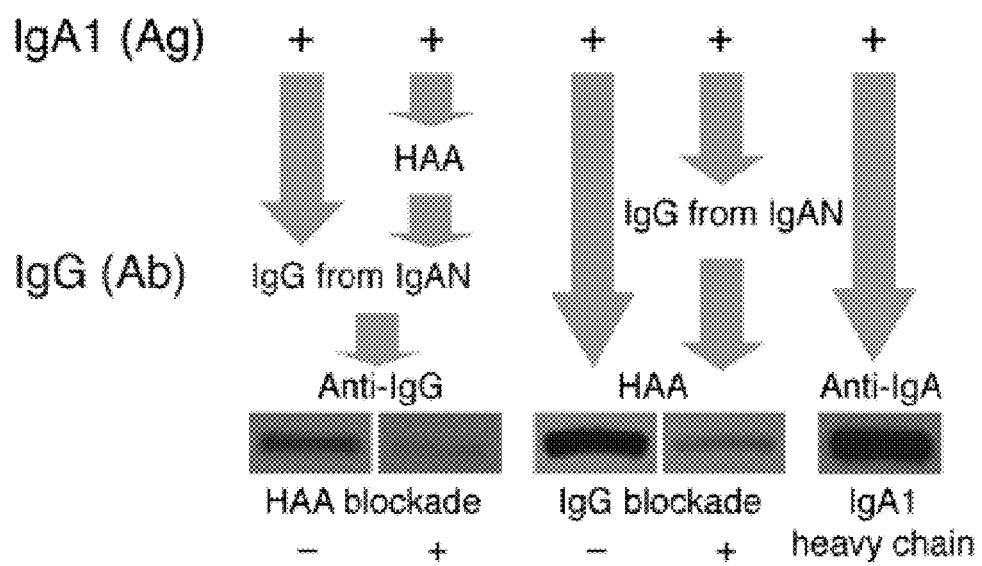
Figure 1D:
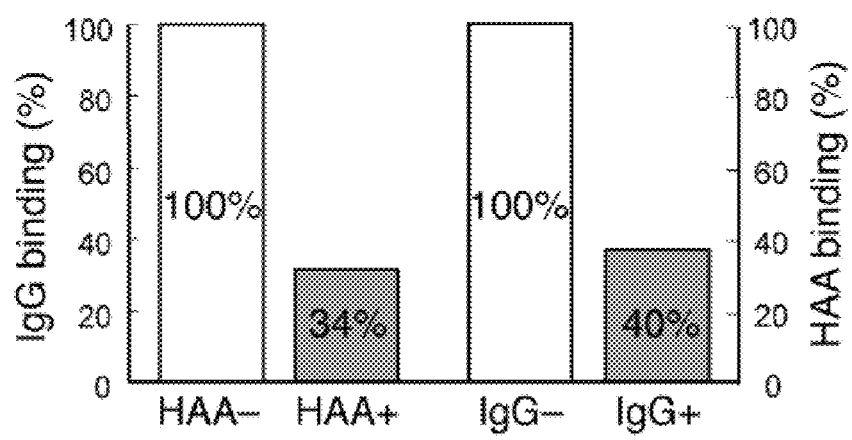

The binding of the serum IgG to Gal-deficient IgA1 was validated by Western blot analysis of the component chains of an enzymatically modified IgA1 myeloma protein (Mce). In each case, the enzymatic modification was confirmed by the binding of the N-acetylgalactosamine-specific (GalNAc-specific) lectin, *Helix aspersa* agglutinin (HAA) (Moore et al., Mol. Immunol. 44:2598-604 (2007); Moldoveanu et al., Kidney Int. 71:1148-54 (2007)). The IgG from the sera of patients with IgAN bound to the heavy chain of the Gal-deficient IgA1, whereas only minimal binding of the IgG from the sera of healthy controls was observed. Removal of the sialic acid from the Gal-deficient IgA1 by neuraminidase treatment resulted in an increase in the binding of the serum IgG from patients with IgAN (FIG. 1A). Desialylated and degalactosylated (dd)-IgA1 bound greater amounts of HAA than did native Gal-deficient IgA1, whereas enzymatically regalactosylated or resialylated dd-IgA1 bound lower amounts of HAA than native Gal-deficient IgA1 (FIG. 1B). The similarity between the extent of binding of the serum IgG and HAA to each of these IgA1 preparations suggested that the binding of serum IgG to the Gal-deficient IgA1 was dependent on the GalNAc moieties (FIG. 1B). This was confirmed by incubation with unlabeled HAA prior to incubation with IgG purified from the serum of an IgAN patient. The preincubation with HAA reduced the binding of the IgG to the Gal-deficient IgA1 by 66% (FIGS. 1C and 1D); conversely, blocking with serum IgG from an IgAN patient reduced the binding of HAA to Gal-deficient IgA1 by 60% (FIGS. 1C and 1D). Thus, the GalNAc in the hinge region of Gal-deficient IgA1 represents a major component of the epitope that is recognized by the IgG specific for Galdeficient IgA1 present in the serum of patients with IgAN.

TABLE 5

Serum levels of antigen-specific IgG. Data are expressed as optical density at 490 nm and shown as means ± SD. dd-IaG1, enzymatically desialylated and degalactosylated IgA1.
Fab-IgA1, Fab fragment of Gd-IgA1 containing part of the hinge region with O-glycans. IgAN, patients with IgA nephropathy; Controls, healthy controls. *, $P < 0.001$, **, $P < 0.0001$.

| Cohort from Southwestern USA | | |
|---|---|---|
| Antigen | IgAN (n = 16) | Controls (n = 16) |
| dd-IgA1 | 2.256 ± 0.112* | 1.995 ± 0.146 |
| Fab-IgA1 | 2.136 ± 0.163* | 1.724 ± 0.184 |

| Cohort from Japan | | |
|---|---|---|
| Antigen | IgAN (n = 20) | Controls (n = 20) |
| Fab-IgA1 | 2.021 ± 0.202** | 1.532 ± 0.229 |

Example 2

Figure 2A:
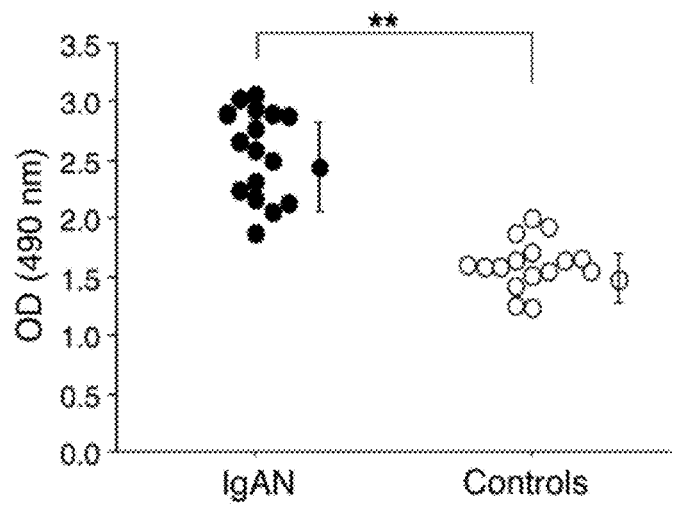
FIGS. 2A to 2C show the characterization of antibodies specific for Gal-deficient IgA1 secreted by cloned cell lines. The levels of antigen-specific IgG produced by IgG-secreting cell lines were measured by capture ELISA. The results are expressed as OD measured at 490 nm.
Figure 2B:
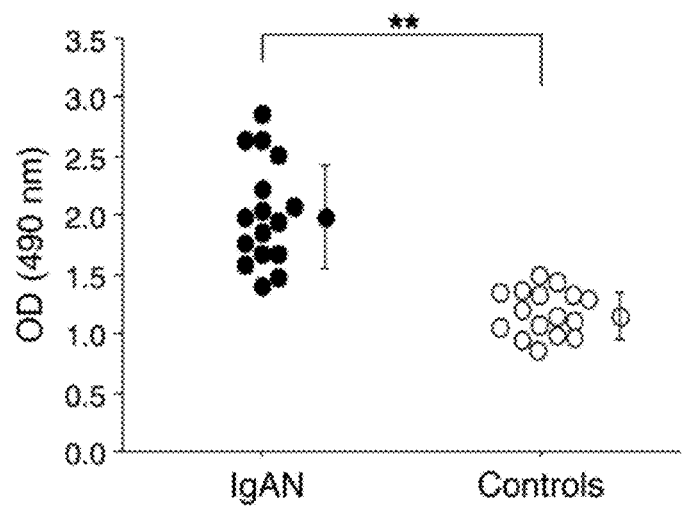
Figure 2C:
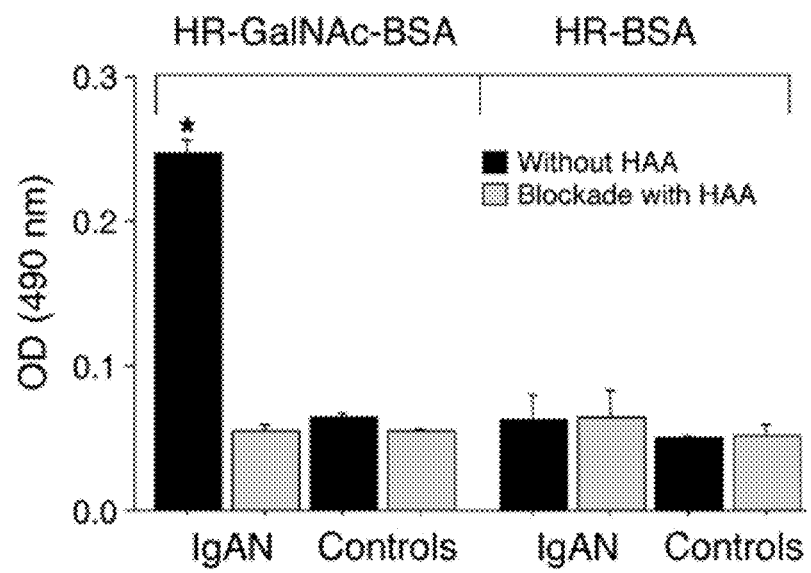

Characterization of Antibodies Specific for Gal-Deficient IgA1 Secreted by IgG-Producing Cell Lines To further characterize the IgG that reacts with the Gal-deficient IgA1, IgG-producing cells were generated by EBV immortalization of B cells isolated from the peripheral blood of the 16 patients with IgAN and 16 healthy controls who had provided blood for measurement of serum IgG specific for Gal-deficient IgA1 (Table 4). After subcloning of the cells, the IgG secreted by the cell lines was characterized by ELISA; the cells derived from IgAN patients produced antibodies that exhibited greater binding to dd-IgA1 and Fab-IgA1 than did the cells derived from controls (P<0.0001) (FIGS. 2A and 2B). Cell lines were randomly selected from 10 IgAN patients and 10 healthy controls and analyzed for the binding of the secreted IgG to a synthetic IgA1 hinge-region peptide linked to BSA (HR-BSA) and a synthetic IgA1 hinge-region glycopeptide linked to BSA with 3 GalNAc residues (HR-GalNAc-BSA) at sites corresponding to the major epitopes of the Gal-deficient IgA1 myeloma protein (Thr228, Ser230, and Ser232) (Novak et al., Contrib. Nephrol. 157:134-8 (2007)). The IgG from the cells derived from IgAN patients did not bind the HR-BSA but bound HR-GalNAc-BSA; moreover, the binding to HR-GalNAc-BSA was inhibited by HAA (78%) (FIG. 2C). Thus, the IgG-secreting cells derived from the peripheral blood of patients with IgAN produced glycan-specific antibodies that recognize Gal-deficient IgA1 in a GalNAc-dependent manner. These IgG-producing cells were further subcloned to isolate single-cell clones producing antibodies specific for Gal-deficient IgA1. 3 cell lines were randomly selected from clones from patients with IgAN (n=16) and 3 cell lines from clones from healthy controls (n=16) and the cultures were scaled up to obtain sufficient amounts of purified IgG for further characterization.

Example 3

Glycan-Specific IgG Forms Immune Complexes with Gal-Deficient IgA1

Figure 3A:
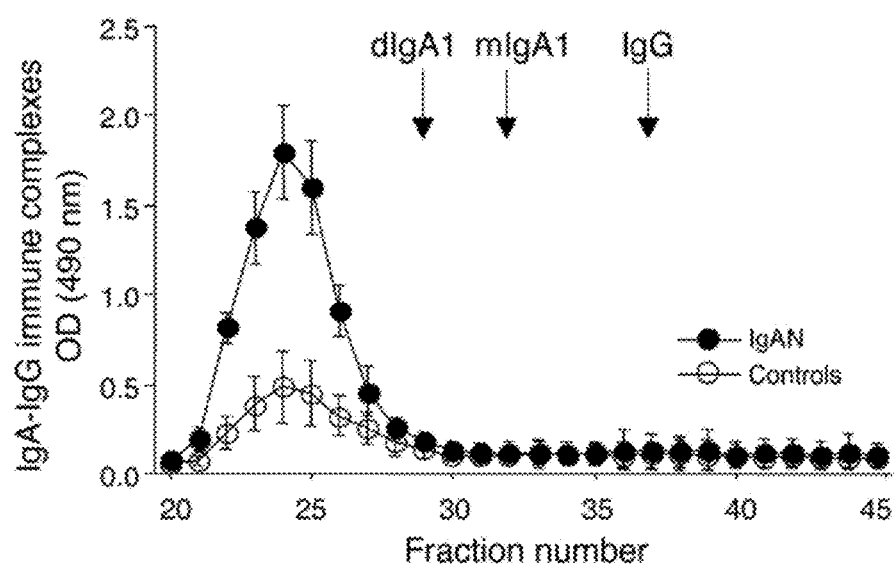
FIGS. 3A to 3C show the characterization of immune-complex formation.

The ability of the glycan-specific antibodies to form immune complexes with Gal-deficient IgA1 was determined in vitro by incubation of the purified IgG proteins with a Gal-deficient IgA1 myeloma protein (Ale mono) at a 1:1 molar ratio. The reaction mixture was then fractionated by HPLC with the IgA1-IgG immune complexes being identified by cross-capture ELISA (Novak et al., Contrib. Nephrol. 157:134-8 (2007)). Incubation of the Gal-deficient IgA1 with IgG produced by the cells derived from IgAN patients resulted in the production of greater amounts of immune complexes than were formed on incubation with IgG produced by cells derived from healthy controls (FIG. 3A). Analysis of the size and composition of the immune complexes suggested that they were composed of 1 molecule of IgG bound to either 1 or 2 molecules of IgA1 (FIG. 3A).

Example 4

Analyses of the IGH, IGκ, and IGλ Genes Derived from Patients with IgAN

Figure 3B:
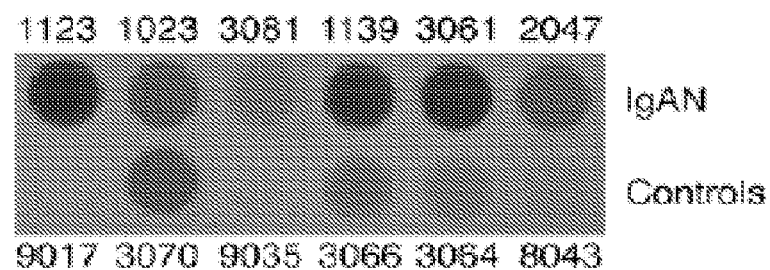
Figure 3C:
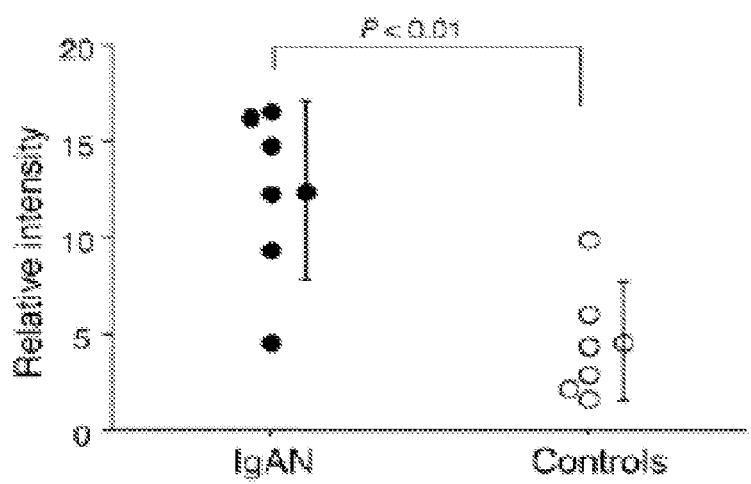

The variable regions of IGH and IGκ or IGλ transcripts from single cells were amplified in 2 rounds of nested RT-PCR reactions using specific primers (Wardemann et al., Science 301:1374-7 (2003)). The resultant amplicons were then purified and directly sequenced. The nucleotide and amino acid sequences for the Ig heavy chains from subjects 1123 and 9017 are given by SEQ ID NOs:75 and 79 and SEQ ID NOs:77 and 81, respectively. The nucleotide and amino acid sequences for the Ig light chains from subjects 1123 and 9017 are given by SEQ ID NOs:76 and 80 and SEQ ID NOs:78 and 81, respectively. The predicted amino acid sequences of the CDR3 of the variable region of the IGH gene (VH genes) from the 7 IgAN patients analyzed differed significantly from the predicted sequences for the genes of the 6 healthy controls that were analyzed (Tables 6 and 7). One of the notable differences was that the 3' end of VH genes from cells of 6 IgAN patients included a sequence encoding YCSR (SEQ ID NO:44) or YCSK (SEQ ID NO:48), which represented an A to S substitution as compared with the sequence encoding YCAR (SEQ ID NO:45) that was identified in 5 of 6 controls (Table 6). In the 1 IgAN patient (subject 3081) who did not have the A to S substitution at this position, there was an R to T substitution at the next position (YCAT (SEQ ID NO:46) vs. YCAR (SEQ ID NO:45)). On dot-blot analysis, extensive binding of the IgG secreted by the cells from the IgAN patients to Gal-deficient IgA1 was found with 1 exception (IgG from the clone from subject 3081; FIG. 3B). The IgG secreted by the cells from the healthy controls either did not bind to Gal-deficient IgA1 or exhibited significantly less binding, again with 1 exception (IgG from the clone from subject 3070 with the sequence YCAS (SEQ ID NO:47)) (FIG. 3B). Densitometric analysis of these blots indicated that the IgG from IgAN patients exhibited greater binding to Gal-deficient IgA1 than did the IgG from healthy controls (FIG. 3C; P<0.01). Thus, the CDR3 of the VH appears to play an important role in the binding of the glycan-specific IgG to the Gal-deficient IgA1, and the A to S substitution found in 6 of 7 patients with IgAN appears to be associated with enhanced binding.

TABLE 6

Comparison of the IgG heavy-chain CDR3 amino acid sequences from the IgAN patients with those from the healthy controls. The amino acid sequences of CDR3 of IgG from 7 IgAN patients and 6 controls. There were notable differences, including a sequence YCSR (SEQ ID NO: 44) or a sequence YCSK (SEQ ID NO: 48) with a change of A to S (bold and underlined S; excluding subject 3081, who had sequence YCAT (SEQ ID NO: 46)) in the CDR3 of heavy chain of IgG from IgAN patients compared with the YCAR (SEQ ID NO: 45) sequence in the controls (except subject 3070; bold S).

| Cell ID | CDR3 (amino acid seq.) |
|---|---|
| Cells from IgAN patients | |
| 1023 | YCSRDLAAFCSGGNCHSVAIDFW (SEQ ID NO: 1) |
| 1123 | YCSKVCRPWNYRRPYYYGMDVW (SEQ ID NO: 2) |
| 1125 | YCSRDRYYCSGGAFDYW (SEQ ID NO: 3) |
| 1139 | YCSRKTSYPPTVGEVRGTSYYYGMDVW (SEQ ID NO: 4) |
| 2047 | YCSKTKFKGYSGFHYW (SEQ ID NO: 5) |
| 3061 | YCSRDRYGLFDYW (SEQ ID NO: 6) |
| 3081 | YCATGDYFGSGTYPIGAFDTW (SEQ ID NO: 7) |
| Cells from healthy controls | |
| 3066 | YCARDLDLW (SEQ ID NO: 8) |
| 3070 | YCASEGHLDYGGNSDAFDIW (SEQ ID NO: 9) |
| 3064 | YCARDVNITATEYYFDYW (SEQ ID NO: 10) |
| 8034 | YCARGNDDYFDYW (SEQ ID NO: 11) |
| 9017 | YCARVQRYDSTGYYPLGYLDLW (SEQ ID NO: 12) |
| 9035 | YCAREWYSYLWDSSYYFDYW (SEQ ID NO: 13) |

TABLE 7

Repertoire and reactivity of antibodies from B cells of patients with IgAN and healthy controls.

| Ig Cell Id | Heavy Chain | | | | | | Light Chain | | | | | React. with Gd-IgA1 |
|---|---|---|---|---|---|---|---|---|---|---|---|---|
| | V | D | J | CDR3 (aa), CDR3 (nt) | L | PI | V | J | CDR3 (aa), CDR3 (nt) | L | PI | |
| Cells from patients with IgAN | | | | | | | | | | | | |
| 1023 | 1-46 | 2-15 | 4 | (SEQ ID NO: 1), (SEQ ID NO: 49) | 20 | 5.61 | 2-29 | κ1 | CMQGIHLPPTVDVF (SEQ ID NO: 14), (SEQ ID NO: 50) | 12 | 6.58 | ± |
| 1123 | 3-23 | 1-7 | 6 | (SEQ ID NO: 2), (SEQ ID NO: 51) | 19 | 9.49 | 2-11 | λ2 | CCSYAGSYTSLF (SEQ ID NO: 15), (SEQ ID NO: 52) | 10 | 13.0 | + |
| 1125 | 3-30 | 3-22 | 4 | (SEQ ID NO: 3), (SEQ ID NO: 53) | 14 | 6.44 | 2-8 | λ2 | CSSYVGSNNSLF (SEQ ID NO: 16), (SEQ ID NO: 54) | 10 | 13.0 | + |
| 1139 | 3-21 | 3-3 | 6 | (SEQ ID NO: 4), (SEQ ID NO: 55) | 24 | 8.83 | 1-40 | λ2 | CQSYDSSLSGYVVF (SEQ ID NO: 17), (SEQ ID NO: 56) | 12 | 13.0 | + |

TABLE 7-continued

Repertoire and reactivity of antibodies from B cells of patients with IgAN and healthy controls.

| Ig Cell Id | Heavy Chain | | | | | | Light Chain | | | | | React. with Gd-IGA1 |
|---|---|---|---|---|---|---|---|---|---|---|---|---|
| | V | D | J | CDR3 (aa), CDR3 (nt) | L | PI | V | J | CDR3 (aa), CDR3 (nt) | L | PI | |
| 2047 | 3-23 | 5-12 | 4 | (SEQ ID NO: 5), (SEQ ID NO: 57) | 13 | 9.84 | 1-5 | κ1 | CQQYNSYPWTF (SEQ ID NO: 18), (SEQ ID NO: 58) | 9 | 13.0 | + |
| 3061 | 3-11 | 5-12 | 4 | (SEQ ID NO: 6), (SEQ ID NO: 59) | 10 | 6.59 | 1-12 | κ2 | CQQANSFPPTGTF (SEQ ID NO: 19), (SEQ ID NO: 60) | 11 | 13.0 | + |
| 3081 | 1-24 | 5-12 | 3 | (SEQ ID NO: 7), (SEQ ID NO: 61) | 18 | 13.0 | 1-39 | κ1 | CQQSYSTPRTF (SEQ ID NO: 20), (SEQ ID NO: 62) | 9 | 9.25 | − |
| Cells from healthy controls | | | | | | | | | | | | |
| 3066 | 4-4 | 3-9 | 4 | (SEQ ID NO: 8), (SEQ ID NO: 63) | 15 | 4.10 | 1-50 | λ2 | CKAWDNSLNAHTVLQAVF (SEQ ID NO: 21), (SEQ ID NO: 64) | 16 | 7.49 | − |
| 3070 | 3-7 | — | 2 | (SEQ ID NO: 9), (SEQ ID NO: 65) | 6 | 4.40 | 3-15 | κ5 | CQQYNNWPQTF (SEQ ID NO: 22), (SEQ ID NO: 66) | 9 | 13.0 | − |
| 3064 | 4-59 | 4-23 | 3 | (SEQ ID NO: 10), (SEQ ID NO: 67) | 17 | 3.92 | 1-39 | κ5 | CQQSYSTPPTF (SEQ ID NO: 23), (SEQ ID NO: 68) | 9 | 13.0 | ± |
| 8034 | 4-39 | 1-1 | 4 | (SEQ ID NO: 11), (SEQ ID NO: 69) | 10 | 4.10 | 3-20 | κ2 | CQQYGSSLYTF (SEQ ID NO: 24), (SEQ ID NO: 70) | 9 | 13.0 | − |
| 9017 | 3-7 | 3-9 | 2 | (SEQ ID NO: 12), (SEQ ID NO: 71) | 19 | 6.58 | 3-9 | λ2 | CQVWDSSSDVVF (SEQ ID NO: 25), (SEQ ID NO: 72) | 10 | 13.0 | − |
| 9035 | 3-7 | 2-8 | 4 | (SEQ ID NO: 13), (SEQ ID NO: 73) | 17 | 4.10 | 3-21 | λ2 | CQVWDSSSDH PF (SEQ ID NO: 26), (SEQ ID NO: 74) | 10 | 4.39 | − |

V, variable;
D, diversity;
J, joint;
L, Length;
+, high reactivity;
±, medium reactivity;
−, no reactivity

Example 5

The Importance of the A to S Substitution in the YCAR/K (SEQ ID NO: 37) Sequence of the CDR3 in the Binding of IgG to Gal-Deficient IgA1

Figure 4A:
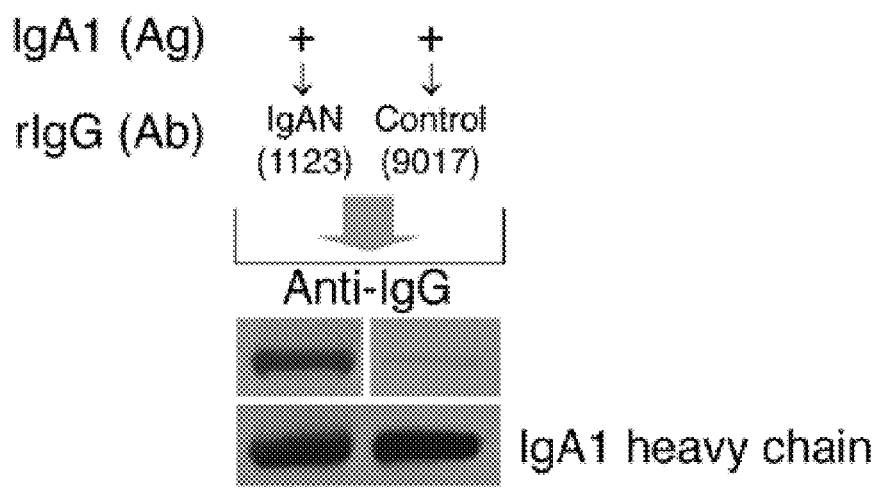
FIGS. 4A to 4D show the importance of the A to S substitution in YCAR (SEQ ID NO:45) or YCAK (SEQ ID NO:37) sequence of CDR3 in the binding of IgG to Gal-deficient IgA1.
Figure 4B:
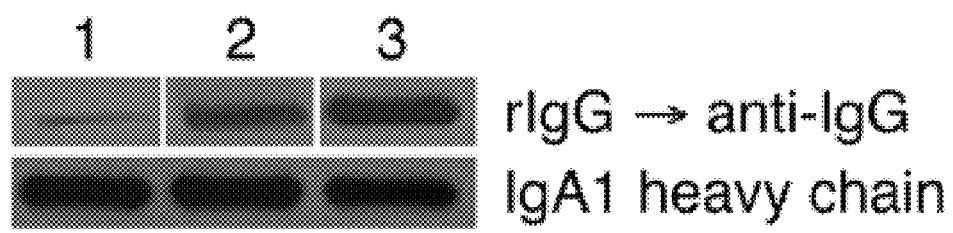

For further analyses, recombinant human IgG (rIgG) was prepared using a single-cell PCR technique to clone the variable regions of the heavy and light chain genes of IgG from an IgG-secreting cell line derived from a patient with IgAN and from an IgG-secreting cell line derived from a healthy control. The corresponding PCR products for heavy and light chains were subcloned into Iv and Igκ or λ expression vectors, respectively, to express rIgG1, also matching the original subclass of the identified antibodies. Western blot analysis demonstrated that the rIgG from the IgAN patient bound to Gal-deficient IgA1 myeloma protein (Ale poly) (FIG. 4A), and this was confirmed by ELISA using Fab-IgA1. Furthermore, the Fab fragment of the rIgG was purified from an IgAN patient to confirm the role of the antigen-binding region in the interaction with Gal-deficient IgA1. ELISA data confirmed that the Fab fragment of rIgG bound to Fab-IgA1 in a fashion similar to that of the intact rIgG. Western blotting against the hinge region of native IgA1, desialylated IgA1, and dd-IgA1 myeloma proteins (Mce1) confirmed that the binding of the rIgG to IgA1 was increased after removal of sialic acid and Gal on the Hinge Region of IgA1 (FIG. 4B).

Figures 4C, 4D:
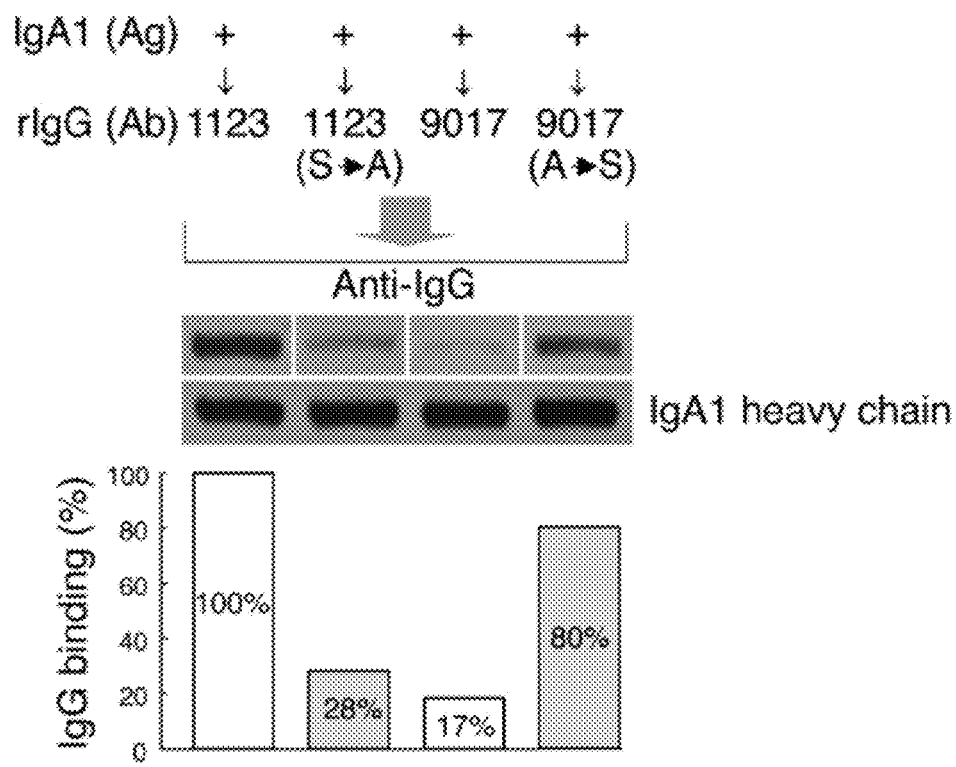

To determine whether the amino acid substitution (A to S) in the CDR3 of the VH domain of IgG from IgAN patients affects the binding to Gal-deficient IgA1, the VH gene of the single-cell line from an IgAN patient (subject 1123) with the YCSKVCRPWNYRRPYYYGMDVW (SEQ ID NO:2) sequence was reverted to the counterpart found in most healthy controls (S to A) (FIG. 4C) using an overlap PCR strategy (Table 4) (Tiller et al., J. Immunol. Methods 329: 112-24 (2008)). Conversely, the CDR3 of the VH gene of the single-cell line from a healthy control (subject 9017) encoding the YCARVQRYDSTGYYPLGYLDLW (SEQ ID NO:12) sequence was mutated (A to S) (FIG. 4C) to generate the sequence found in most of the IgAN patients. Both mutations were confirmed by sequencing after cloning into an IgG-expressing vector, as described above. The rIgG was then purified and tested for binding to Gal-deficient IgA1 using Western blotting and ELISA. The S to A change in the CDR3 of the IgG of the IgAN patient reduced the binding of rIgG to Gal-deficient IgA1 by 72%. Conversely, the A to S substitution in CDR3 of the IgG of a healthy control increased binding to Gal-deficient IgA1 to 80% of that of the rIgG of the IgAN patient (FIG. 4D). These data were confirmed by ELISA using Fab-IgA1 as the antigen.

Example 6

Figure 5A:
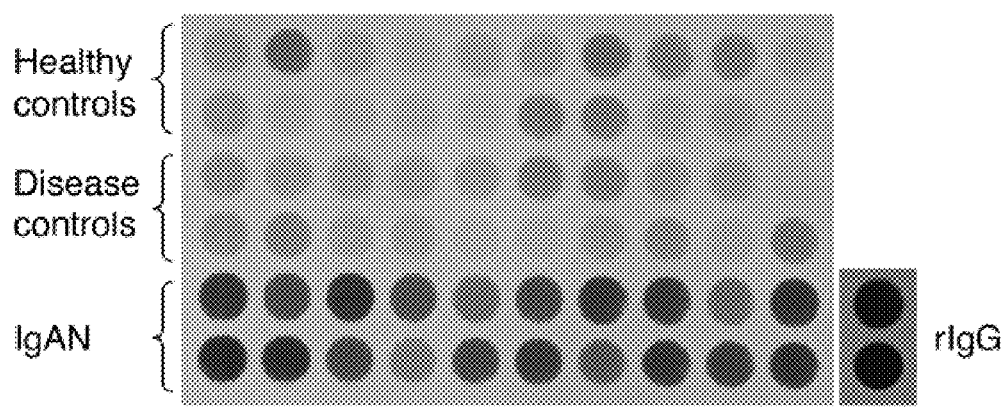
FIGS. 5A to 5E show serum levels of IgG specific for Gal-deficient IgA1 are elevated in patients with IgAN.
Figure 5B:
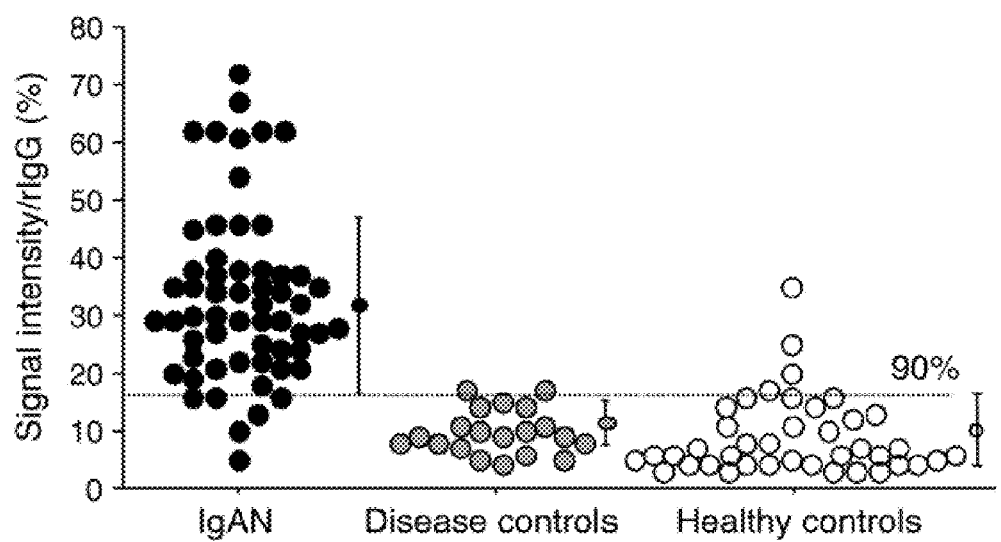
Figure 5C:
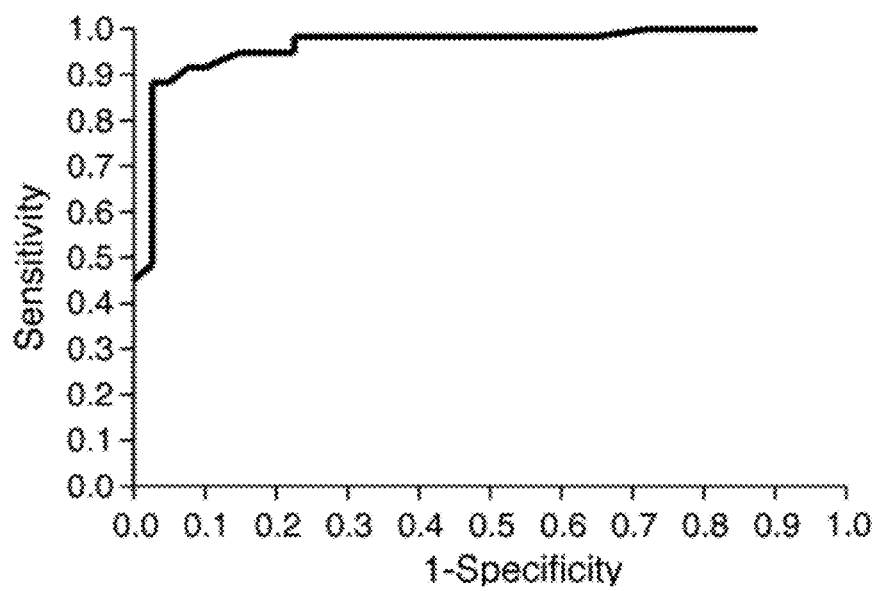
Figure 5D:
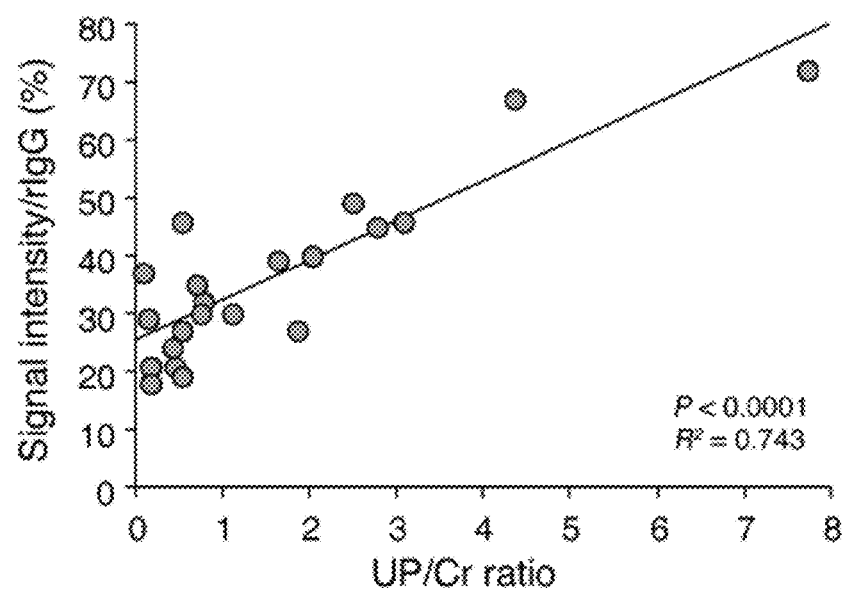
Figure 5E:
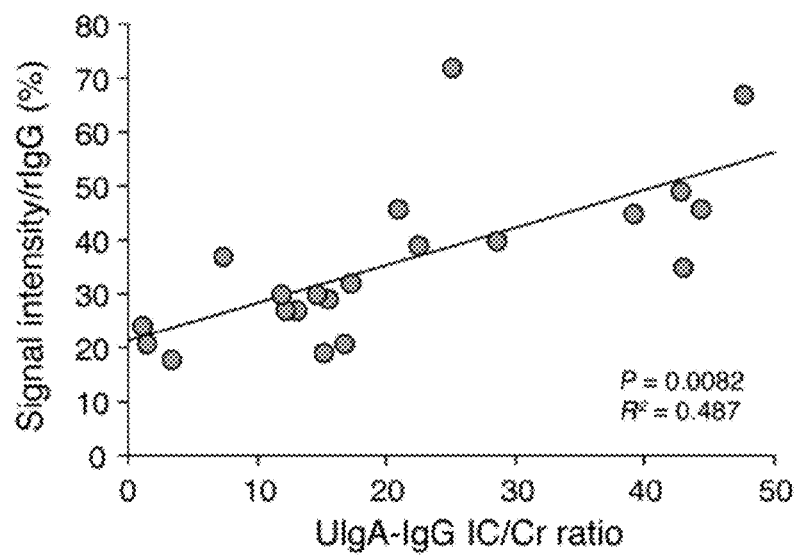

Serum Levels of IgG Specific for Gal-Deficient IgA1 are Elevated in Patients with IgAN As patients with IgAN were found to have higher levels of circulating IgG antibodies with specificity for Gal-deficient IgA1, the quantitative differences were evaluated using a novel dot-blot assay that was developed for this purpose. The IgAN patients (n=60) were found to have elevated levels of serum IgG specific for Gal-deficient IgA1 as compared with disease controls (n=20) and healthy controls (n=40) (FIGS. 5A and 5B). The relative intensity values for the serum IgG antibodies from IgAN patients in both cohorts, disease controls, and healthy controls were 33.2±14.6, 9.9±3.9, and 9.0±6.8, respectively (FIG. 5B; $P<0.0001$). To test the reproducibility of this assay, the same serum samples were reanalyzed twice, and the difference between the experiments was 3.5%±2.3%. Notably, 54 of the 60 patients with IgAN had mean binding values higher than the 90th percentile of those for healthy controls. A receiver operating characteristic (ROC)-curve analysis indicated the area under the curve was 0.9644 (FIG. 5C; $P<0.0001$); when the level of serum IgG specific for Gal-deficient IgA1 specificity reached 95.0%, the corresponding sensitivity was 88.3%. Furthermore, for 20 IgAN patients with urine and blood samples collected within 30 days of renal biopsy (contemporaneous samples), possible correlations were assessed among clinical and laboratory findings. The results of these analyses showed that the intensity of binding of IgG to Gal-deficient IgA1 as determined by the dot-blot analysis correlated with proteinuria (expressed as urinary protein/urinary creatinine [UP/Cr] ratio; FIG. 5D; $P<0.0001$) as well as with urinary IgA-IgG immune complexes (expressed relative to Cr concentration; FIG. 5E; $P=0.0082$).

Example 7

Measurement of Serum Levels of Galactose-Deficient IgA1 and Anti-Glycan IgG Antibodies Pre- and Post-Diagnosis of IgA Nephropathy (IgAN)

The Department of Defense Serum Repository was utilized to evaluate serum levels of galactose-deficient IgA1 (Gd-IgA1) and antibodies specific for the hinge-region glyucans of Gd-IgA1 in serially collected serum samples from service personnel prior to IgAN diagnosis. These results were then compared to age-, sex-, race-, and age-of-serum-sample-matched healthy controls. The repository stores over 40 million samples, which have been collected from active-duty soldiers approximately every one to two years since 1985. The initial serum samples are banked at the time of entry into the military when soldiers must pass a medical evaluation, that includes a history, a physical examination, vital signs, urinalysis, and laboratory testing. With normal findings, it is presumed that the soldiers do not have even subclinical evidence of renal disease at the time of enlistment.

In a pilot study, eight subjects with IgAN without crescents on biopsy or clinical evidence of rapidly progressive glomerulonephritis (RPGN) were compared to twenty-four matched healthy controls. The earliest available sample, the second-to-last sample, and the last sample prior to diagnosis were processed. For subgroup analysis, the subjects were divided into 2 groups: 4 subjects with mild IgAN and 4 subjects with moderate IgAN, based on serum creatinine concentration, quantification of proteinuria, and level of activity on histology.

The IgAN patients had a higher mean serum Gd-IgA1 level prior to diagnosis than did healthy controls (136.7 vs. 79.2 U/mL; p=0.002). The Gd-IgA1 levels were measured with standard galactose-deficient IgA1 (Ale) as described in Suzuki et al., J. Clin. Invest. 118:629-39 (2008). For the IgAN patients, the mean serum Gd-IgA1 levels were significantly higher than for the healthy controls mean levels in subsets of samples at less than 1000 days and greater than 1000 days prior to diagnosis (138.2 vs. 81.4 U/mL; p=0.019 and 134.5 vs. 76.7 U/mL; p=0.046 respectively). Based on an ROC curve with an area of 0.731 with a threshold of 91 U/mL, the assay achieved 67% sensitivity and 78% specificity. The mean change in serum Gd-IgA1 levels over the change in time for the IgAN patients was higher than for the healthy controls (0.017 vs. 0.00086 U/mL/day; p=0.006).

In a subgroup analysis, patients with moderate IgAN had a higher mean serum Gd-IgA1 level prior to diagnosis than did patients with mild IgAN (170.6 v. 98.2 U/mL; p=0.03).

In addition, the eight IgAN patients had a higher mean serum level of antibody specific for the hinge-region glycans of Gd-IgA1 compared to that for the healthy controls (55 vs. 26; p=0.03). A threshold value of 40 was 100% sensitive and specific.

The results demonstrate that the serum Gd-IgA1 level is elevated years prior to diagnosis of IgAN and that it rises during the interval prior to diagnosis. In addition, a higher Gd-IgA1 level may be associated with more severe IgAN.

This information can aid in the diagnosis of IgAN in patients with urinary abnormalities or other signs of kidney disease that are at too high a risk for renal biopsy. In addition, this assay can distinguish between IgAN patients that will have a benign clinical course without chronic progression to chronic kidney damage (approximately 50% of subjects) from those that will ultimately develop end-stage kidney disease (approximately 40% of subjects). This information could influence the length of the follow-up intervals and timing of medical intervention.

Example 8

Figure 6A:
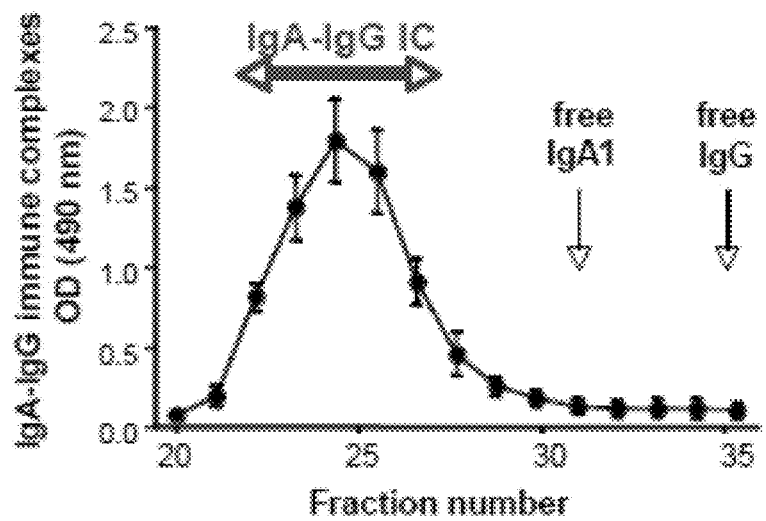
FIGS. 6A-6C show the characterization of a passive murine model of IgAN using immune complexes formed between Gal-deficient IgA1 and anti-glycan IgG.
Figure 6B:
Figure 6C:
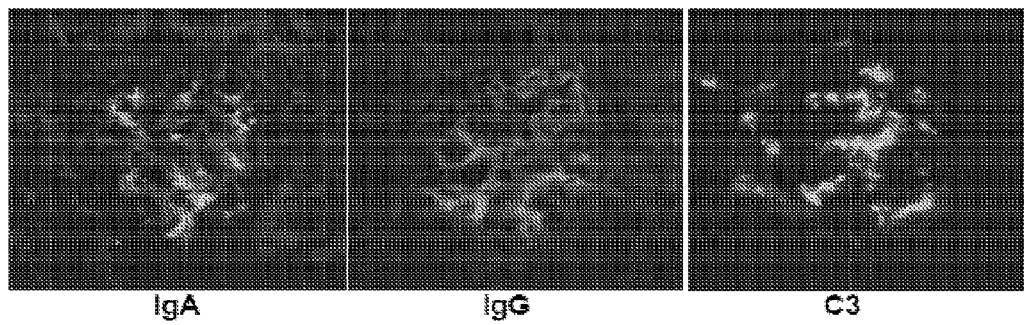
Figure 7:
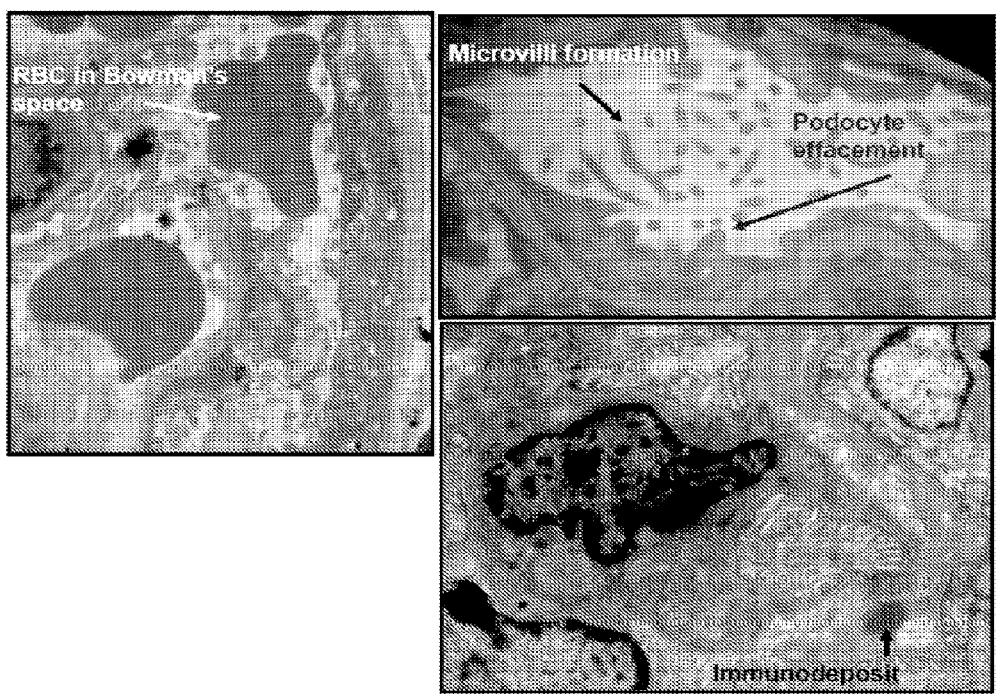
FIG. 7 shows transmission electron microscopic images of glomeruli of mice injected with Gal-deficient IgA1-IgG complexes. The images showed electron-dense immunodeposits (bottom right) in the mesangium and evidence of podocyte injury (podocyte effacement, microvilli formation; top right) and the presence of a red blood cell in Bowman's urinary space (top left), concurrent with hematuria and proteinuria.

Characterization of a Passive Model of IgAN Using Immune Complexes Formed Between Gal-Deficient IgA1 and Anti-Glycan IgG To develop a passive model of IgAN, immune complexes were formed in vitro using Gal-deficient IgA1 and anti-glycan IgG purified from a patient with IgAN (FIG. 6A). The immune complexes were injected intravenously into nude mice. The complexes deposited in the renal mesangium (FIG. 6C), together with murine C3, and induced hematuria and proteinuria. Scanning electron microscopy (EM) confirmed the presence of red blood cells (RBC) in the urine of mice injected with these immune complexes (FIG. 6B). Albuminuria increased by ~50% 24 hours after injection of the complexes, concurrently with hematuria. Examination of the renal tissue by transmission EM confirmed electron-dense deposits in the mesangium and showed evidence of podocyte injury (podocyte effacement, microvilli formation) and presence of RBC in Bowman's urinary space (FIG. 7). In control experiments, using IgA or IgG alone or IgG from a healthy control with Gal-deficient IgA1 that did not form pathogenic immune complexes, no evidence of IgG or murine C3 renal deposition or development of hematuria or proteinuria was observed. Gal-deficient IgA1, but not fully galactosylated IgA1, deposited only transiently and did not cause any tissue injury.

Example 9

Figure 8:
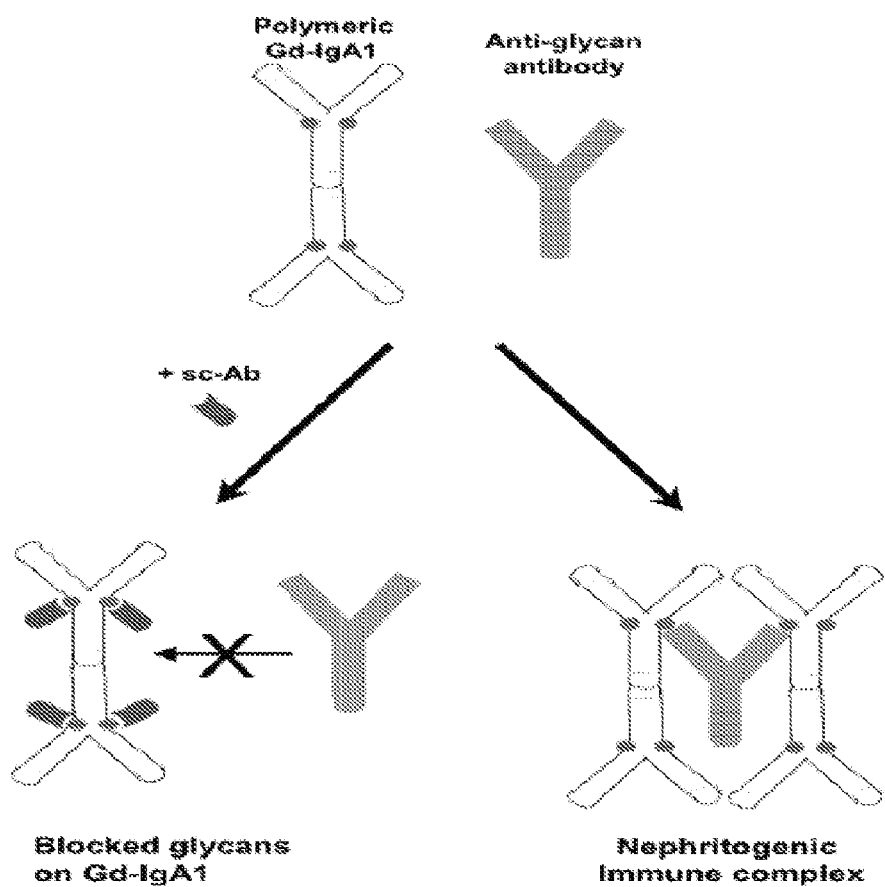
FIG. 8 shows an immunologically-mediated strategy for preventing the formation of large, nephritogenic immune complexes in IgAN. Antigenic glycan determinants in the hinge region of IgA1 are covered with monovalent, high-affinity single chain (sc)-Abs or other monovalent antibody fragments (such as Fab or Fv) that prevent naturally-occurring anti-GalNAc antibodies from cross-linking polymeric Gd-IgA1 molecules. Only small, non-nephritogenic complexes are formed.

Treatment of IgA Nephropathy (IgAN) with Anti-Glycan Antibodies and/or Glycopeptides Capable of Blocking Galactose-Deficient IgA (Gd-IgA) Binding to IgG Blocking the formation of nephritogenic high-molecular weight circulatory immune complexes (CIC) from circulating Gd-IgA1 and the conversion of active immune complexes into inactive immune complexes reduces the deposition in the renal mesangium, thus lessening or preventing glomerular injury. The therapeutic goal is achieved with monovalent anti-glycan reagents, such as single-chain antibodies (sc-Abs) that bind Gd-IgA1 as shown in FIG. 8.

To create sc-Abs that bind Gd-IgA1, a phage-display library of sc-Abs obtained from immortalized B lymphocytes from IgAN patients with active disease, patients in long-term remission, and healthy controls is made. To make the phage-display library, cells expressing antibodies specific for Gd-IgA1 are isolated. The antibodies specific for Gd-IgA1 are isolated from these cells, and the corresponding population of $V_H$ and $V_L$ regions are cloned. These clones are then expressed as sc-Abs in a phage-display library, and the clones with high-affinity for Gd-IgA1 are selected.

The high-affinity sc-Abs are then expressed in vitro to determine their ability to block binding of serum anti-glycan antibodies to Gd-IgA1. The selected sc-Abs are produced in a yeast expression system. Using cultured mesangial cells (MC), the sc-Abs are tested for their ability to block the formation of pathogenic IgA1-containing immune complexes in the presence of anti-glycan Abs from the sera of IgAN patients.

The high-affinity sc-Abs are then tested in the passive murine model of IgAN for their capacity to prevent glomerular deposition of immune complexes and renal injury. The passive murine model of IgAN, as described above, is based on injection of immune complexes formed from human Gd-IgA1 and anti-glycan Abs. These immune complexes deposit in the mesangium together with murine C3 to induce pathological and clinical changes typical of human IgAN, including hematuria and proteinuria. The high-affinity sc-Abs are injected intravenously into the passive murine model and glomerular deposition of the pathogenic immune complexes is monitored.

Generation of immunologically highly specific reagents that recognize, with high selectivity, peripheral-blood B cells and lymphoblasts expressing Gd-IgA1 on their cell surfaces is useful for non-invasive diagnostic purposes to monitor the kinetics of appearance and enumeration of cells ultimately producing Gd-IgA1. Whether the sc-Abs with high affinity and specificity for Gd-IgA1 can selectively suppress differentiation of cells producing Gd-IgA1 molecules is tested using peripheral blood mononuclear cells from IgAN patients and healthy controls stimulated in vitro with pokeweed mitogen in the presence and absence of sc-Abs with high specificity and affinity for Gd-IgA1. The suppression of Gd-IgA1 production is evaluated at the humoral level (secreted IgA1 antibody) and cellular level (enumeration of cells secreting Gd-IgA1) using HAA-dependent assays previously described (Moldoveanu et al., Kidney Int. 71:134-8 (2007); Suzuki et al., J. Clin. Invest. 118:629-39 (2008)).

Figure 9:
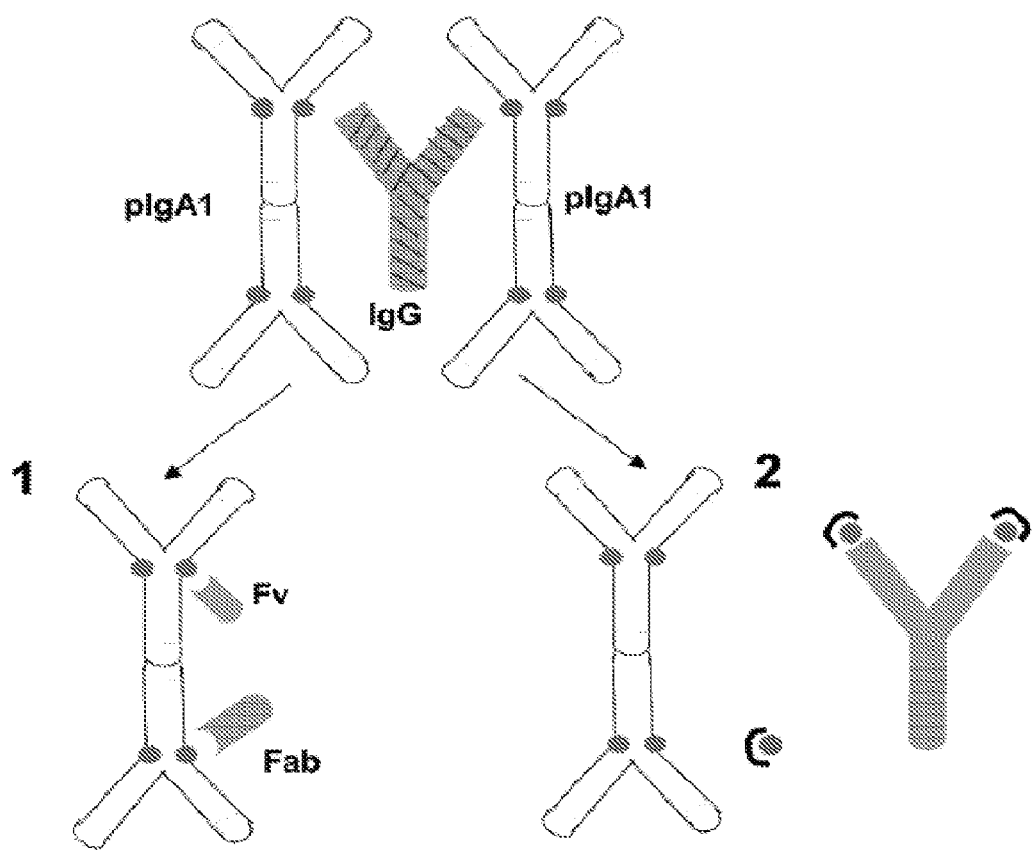
FIG. 9 shows two immunologically-mediated strategies for preventing the formation of large nephritogenic immune complexes in IgA nephropathy. In strategy 1, antigenic determinants in the hinge-region glycans are covered with monovalent, high-affinity Fv or Fab fragments of antibodies that prevent naturally-occurring anti-GalNAc IgG or IgA1 antibodies from cross-linking Gal-deficient polymeric IgA molecules. In strategy 2, a synthetic glycopeptide with a single GalNAc residue (to prevent cross-linking) is recognized by naturally occurring IgG (or IgA1) anti-GalNAc antibodies that cannot cross-link Gal-deficient polymeric IgA1. In both cases, small, non-nephritogenic complexes are formed.

Another approach for preventing the formation of pathogenic immune complexes is the use of synthetic glycopeptides. For example, for the immune complexes of interest in patients with IgAN, a single GalNAc residue prevents cross-linking of the galactose-deficient IgA1 by an intact IgG molecule with 2 antigen-binding sites. The glycopeptide is recognized by these naturally occurring IgG (or IgA) anti-GalNAc antibodies, thereby inhibiting binding to the galactose-deficient polymeric IgA1. Thus, large pathogenic immune complexes that are capable of inducing renal injury (nephritogenic complexes) are not formed (FIG. 9, part 2). Competition for binding of the glycan-specific IgG antibodies to the galactose-deficient IgA1 is also accomplished by using monovalent, non-cross-linking Fab or Fv fragments of anti-glycan antibodies to bind to the exposed GalNAc residue in the hinge region of the galactose-deficient IgA1 (FIG. 9, part 1).

What is claimed is:

1. A method of treating IgA nephropathy in a subject, the method comprising:
   a. obtaining a biological sample from a subject;
   b. determining a level of IgG, IgA1, or both IgG and IgA1 specific for the hinge region of a galactose-deficient IgA1 in the sample;
   c. determining a level of galactose-deficient IgA1 in the sample, wherein an increase in the level of IgG, IgA1, or both IgG and IgA1 specific for the hinge region of galactose-deficient IgA1 and an increase in the level of galactose-deficient IgA1 in the sample as compared to a control indicates the subject has or is at risk of developing IgA nephropathy, wherein the level of galactose-deficient IgA1 in the subject is detected using an antibody specific for a galactose-deficient hinge-region O-linked glycan of IgA1; and
   d. treating the IgA nephropathy in the subject.

2. The method of claim 1, wherein the IgG, IgA1, or both IgG and IgA1 are isolated from a B cell in the sample.

3. The method of claim 2, wherein the B cell is isolated from a population of peripheral blood mononuclear cells (PBMCs) in the sample.

4. The method of claim 3, wherein the B cell is immortalized.

5. The method of claim 4 wherein the B cell is immortalized by transformation with an Epstein-Barr virus (EBV).

6. The method of claim 1, wherein the antibody is a monoclonal antibody.

7. The method of claim 1, wherein the IgG, IgA1, or both IgG and IgA1 specific for the hinge region of a galactose-deficient IgA1 in the sample comprises an alanine to serine amino acid substitution in a complementarity determining region 3 (CDR3) of an immunoglobulin heavy chain (IGH) variable region.

* * * * *

UNITED STATES PATENT AND TRADEMARK OFFICE
CERTIFICATE OF CORRECTION

PATENT NO. : 9,655,963 B2  
APPLICATION NO. : 14/318082  
DATED : May 23, 2017  
INVENTOR(S) : Suzuki et al.

Page 1 of 1

It is certified that error appears in the above-identified patent and that said Letters Patent is hereby corrected as shown below:

In the Specification

Column 1, Lines 17-20, Delete:
"This invention was made with government funding under Grant Nos. 1 RO1 DK078244 and 1 PO1 DK61525 from the National Institutes of Health. The government has certain rights in this invention."
And Insert:
--This invention was made with government support under grant numbers DK078244 and DK061525 awarded by the National Institutes of Health. The government has certain rights in the invention.--

Signed and Sealed this
Twenty-fourth Day of September, 2019

Andrei Iancu
*Director of the United States Patent and Trademark Office*